United States Patent
Warnick

(10) Patent No.: US 7,686,835 B2
(45) Date of Patent: Mar. 30, 2010

(54) PEDICLE SCREW SYSTEM WITH PROVISIONAL LOCKING ASPECTS

(75) Inventor: David R. Warnick, Spanish Fork, UT (US)

(73) Assignee: X-spine Systems, Inc., Miamisburg, OH (US)

( * ) Notice: Subject to any disclaimer, the term of this patent is extended or adjusted under 35 U.S.C. 154(b) by 478 days.

(21) Appl. No.: 11/543,348

(22) Filed: Oct. 4, 2006

(65) Prior Publication Data

US 2007/0093827 A1   Apr. 26, 2007

Related U.S. Application Data

(60) Provisional application No. 60/723,498, filed on Oct. 4, 2005.

(51) Int. Cl.
*A61F 2/30* (2006.01)
(52) U.S. Cl. .............. 606/264; 606/265; 606/267; 606/272; 606/300; 606/305
(58) Field of Classification Search ......... 606/264–278, 606/300–321; 411/190, 337, 439, 511, 955
See application file for complete search history.

(56) References Cited

U.S. PATENT DOCUMENTS

| | | | |
|---|---|---|---|
| 483,342 A | 9/1892 | Bolte | |
| 900,717 A | 10/1908 | Feaster | |
| 2,344,381 A | 3/1944 | Young | |
| 3,019,504 A | 2/1962 | Castagliuolo | |
| 3,648,691 A | 3/1972 | Lumb et al. | |
| 3,752,203 A | 8/1973 | Hill, Jr. | |
| 3,875,936 A | 4/1975 | Volz | |
| 4,011,602 A | 3/1977 | Rybicki et al. | |
| 4,085,744 A | 4/1978 | Lewis et al. | |
| 4,269,178 A | 5/1981 | Keene | |
| 4,289,124 A | 9/1981 | Zickel | |
| 4,294,300 A | 10/1981 | Bouwman | |
| 4,309,139 A | 1/1982 | Nakae | |
| 4,411,259 A | 10/1983 | Drummond | |
| 4,604,995 A | 8/1986 | Stephens et al. | |
| 4,611,580 A | 9/1986 | Wu | |
| 4,611,581 A | 9/1986 | Steffee | |
| 4,641,636 A | 2/1987 | Cotrel | |

(Continued)

FOREIGN PATENT DOCUMENTS

DE   3219575 A1   12/1983

(Continued)

OTHER PUBLICATIONS

Expedium Spine System, DePuy Spine, Raynham, MA 02767.

*Primary Examiner*—Eduardo C Robert
*Assistant Examiner*—Christina Negrelli
(74) *Attorney, Agent, or Firm*—Jacox, Meckstroth & Jenkins

(57) ABSTRACT

A tulip assembly configured to be coupled to a head of a bone fixation device includes at least one inner member configured to fix the tulip assembly to the head of a bone fixation device, and an outer member including at least one engagement surface configured to selectively fix a rod in the tulip assembly via rotation of the outer member, wherein the fixation of the tulip assembly to the head of the bone fixation device is independent of the fixation of a rod in the tulip assembly.

21 Claims, 14 Drawing Sheets

U.S. PATENT DOCUMENTS

| | | |
|---|---|---|
| 4,648,388 A | 3/1987 | Steffee |
| 4,653,481 A | 3/1987 | Howland et al. |
| 4,655,199 A | 4/1987 | Steffee |
| 4,658,809 A | 4/1987 | Ulrich et al. |
| 4,696,290 A | 9/1987 | Steffee |
| 4,719,905 A | 1/1988 | Steffee |
| 4,763,644 A | 8/1988 | Webb |
| 4,771,767 A | 9/1988 | Steffee |
| 4,805,602 A | 2/1989 | Puno et al. |
| 4,815,453 A | 3/1989 | Cotrel |
| 4,887,595 A | 12/1989 | Heinig et al. |
| 4,887,596 A | 12/1989 | Sherman |
| 4,913,134 A | 4/1990 | Luque |
| 4,946,458 A | 8/1990 | Harms et al. |
| 4,950,269 A | 8/1990 | Gaines |
| 5,005,562 A | 4/1991 | Cotrel |
| 5,024,213 A | 6/1991 | Asher et al. |
| 5,042,982 A | 8/1991 | Harms et al. |
| 5,067,955 A | 11/1991 | Cotrel |
| 5,084,049 A | 1/1992 | Asher et al. |
| 5,092,867 A | 3/1992 | Harms et al. |
| 5,113,685 A | 5/1992 | Asher et al. |
| 5,120,171 A | 6/1992 | Lasner |
| 5,127,912 A | 7/1992 | Ray et al. |
| 5,129,900 A | 7/1992 | Asher et al. |
| 5,176,680 A | 1/1993 | Vignaud et al. |
| 5,183,359 A | 2/1993 | Barth |
| 5,190,543 A | 3/1993 | Schlapfer |
| 5,207,678 A | 5/1993 | Harms et al. |
| 5,257,993 A | 11/1993 | Asher et al. |
| 5,261,913 A | 11/1993 | Marnay |
| 5,312,402 A | 5/1994 | Schlapfer |
| 5,346,493 A | 9/1994 | Stahurski et al. |
| 5,360,431 A | 11/1994 | Puno et al. |
| 5,380,325 A | 1/1995 | Lahille et al. |
| 5,466,237 A | 11/1995 | Byrd, III et al. |
| 5,474,555 A | 12/1995 | Puno et al. |
| 5,520,689 A | 5/1996 | Schlapfer |
| 5,549,608 A | 8/1996 | Errico et al. |
| 5,562,663 A | 10/1996 | Wisnewski et al. |
| 5,603,714 A | 2/1997 | Kaneda et al. |
| 5,609,593 A | 3/1997 | Errico et al. |
| 5,624,442 A | 4/1997 | Mellinger et al. |
| 5,647,873 A | 7/1997 | Errico et al. |
| 5,667,508 A | 9/1997 | Errico et al. |
| 5,669,911 A | 9/1997 | Errico et al. |
| 5,690,630 A | 11/1997 | Errico et al. |
| 5,797,911 A | 8/1998 | Sherman et al. |
| 5,817,094 A | 10/1998 | Errico et al. |
| 5,879,350 A | 3/1999 | Sherman |
| 5,882,350 A | 3/1999 | Ralph |
| 5,885,286 A | 3/1999 | Sherman et al. |
| 5,891,145 A | 4/1999 | Morrison et al. |
| 5,954,725 A | 9/1999 | Sherman |
| 6,010,503 A | 1/2000 | Richelsoph |
| 6,063,090 A | 5/2000 | Schlapfer |
| 6,077,262 A | 6/2000 | Schlapfer et al. |
| 6,090,111 A | 7/2000 | Nichols |
| 6,113,601 A | 9/2000 | Tatar |
| 6,132,432 A | 10/2000 | Richelsoph |
| 6,235,033 B1 | 5/2001 | Brace et al. |
| 6,280,442 B1 | 8/2001 | Barker et al. |
| 6,302,888 B1 | 10/2001 | Mellinger et al. |
| RE37,665 E | 4/2002 | Ralph |
| 6,371,957 B1 | 4/2002 | Amrein et al. |
| 6,402,752 B2 | 6/2002 | Schaffler-Wachter |
| 6,451,021 B1 | 9/2002 | Ralph et al. |
| 6,475,218 B2 | 11/2002 | Gournay et al. |
| 6,488,681 B2 | 12/2002 | Martin et al. |
| 6,623,485 B2 | 9/2003 | Doubler et al. |
| 6,626,908 B2 | 9/2003 | Cooper et al. |
| 6,652,526 B1 | 11/2003 | Arafiles |
| 6,660,004 B2 | 12/2003 | Barker et al. |
| 6,716,214 B1 | 4/2004 | Jackson |
| 6,730,089 B2 | 5/2004 | Jackson |
| 6,730,093 B2 | 5/2004 | Saint Martin |
| 6,755,829 B1 | 6/2004 | Bono et al. |
| 6,786,903 B2 | 9/2004 | Lin |
| 6,793,657 B2 | 9/2004 | Lee et al. |
| 6,802,844 B2 | 10/2004 | Ferree |
| 6,827,719 B2 | 12/2004 | Ralph et al. |
| 6,840,940 B2 | 1/2005 | Ralph et al. |
| 6,843,791 B2 | 1/2005 | Serhan |
| 6,858,030 B2 | 2/2005 | Martin et al. |
| 6,869,433 B2 | 3/2005 | Glascott |
| 6,896,677 B1 | 5/2005 | Lin |
| 7,022,122 B2 | 4/2006 | Amrein |
| 7,081,117 B2 | 7/2006 | Bono et al. |
| 7,083,621 B2 | 8/2006 | Shaolian et al. |
| 7,125,426 B2 | 10/2006 | Moumene et al. |
| 7,141,051 B2 | 11/2006 | Janowski et al. |
| 7,261,715 B2 | 8/2007 | Rezach et al. |
| 7,291,151 B2 | 11/2007 | Alvarez |
| 7,291,153 B2 | 11/2007 | Glascott |
| 7,294,128 B2 | 11/2007 | Alleyne et al. |
| 7,322,981 B2 | 1/2008 | Jackson |
| 7,338,491 B2 | 3/2008 | Baker et al. |
| 7,377,923 B2 | 5/2008 | Purcell et al. |
| 2002/0013585 A1 | 1/2002 | Gournay et al. |
| 2002/0026193 A1 | 2/2002 | Barker et al. |
| 2002/0082601 A1 | 6/2002 | Toyama et al. |
| 2002/0091386 A1 | 7/2002 | Martin et al. |
| 2002/0111626 A1 | 8/2002 | Ralph et al. |
| 2002/0120272 A1 | 8/2002 | Yuan et al. |
| 2002/0133154 A1 | 9/2002 | Saint Martin |
| 2002/0133158 A1 | 9/2002 | Saint Martin |
| 2002/0143341 A1* | 10/2002 | Biedermann et al. ......... 606/73 |
| 2002/0151900 A1 | 10/2002 | Glascott |
| 2002/0183748 A1 | 12/2002 | Martin et al. |
| 2003/0073996 A1 | 4/2003 | Doubler et al. |
| 2003/0078583 A1 | 4/2003 | Biedermann et al. |
| 2003/0187433 A1 | 10/2003 | Lin |
| 2003/0187434 A1 | 10/2003 | Lin |
| 2003/0199873 A1 | 10/2003 | Richelsoph |
| 2004/0039383 A1 | 2/2004 | Jackson |
| 2004/0039384 A1 | 2/2004 | Boehm |
| 2004/0049190 A1 | 3/2004 | Biedermann et al. |
| 2004/0097933 A1 | 5/2004 | Lourdel et al. |
| 2004/0116929 A1 | 6/2004 | Barker et al. |
| 2004/0127896 A1 | 7/2004 | Lombardo et al. |
| 2004/0138662 A1 | 7/2004 | Landry et al. |
| 2004/0153068 A1 | 8/2004 | Janowski et al. |
| 2004/0172020 A1 | 9/2004 | Beaurain et al. |
| 2004/0172022 A1 | 9/2004 | Landry et al. |
| 2004/0236330 A1 | 11/2004 | Purcell et al. |
| 2004/0249380 A1 | 12/2004 | Glascott |
| 2004/0267264 A1 | 12/2004 | Konieczynski et al. |
| 2005/0033296 A1 | 2/2005 | Bono et al. |
| 2005/0049589 A1 | 3/2005 | Jackson |
| 2005/0113830 A1 | 5/2005 | Rezach et al. |
| 2005/0131410 A1 | 6/2005 | Lin |
| 2005/0177154 A1 | 8/2005 | Moumene et al. |
| 2005/0177157 A1 | 8/2005 | Jahng |
| 2005/0182400 A1 | 8/2005 | White |
| 2005/0187548 A1 | 8/2005 | Butler et al. |
| 2005/0192570 A1 | 9/2005 | Jackson |
| 2005/0192571 A1 | 9/2005 | Abdelgany |
| 2005/0192573 A1 | 9/2005 | Abdelgany |
| 2005/0203515 A1 | 9/2005 | Doherty et al. |
| 2005/0203516 A1 | 9/2005 | Biedermann et al. |
| 2005/0203519 A1 | 9/2005 | Harms et al. |
| 2005/0215998 A1 | 9/2005 | Donath |
| 2005/0215999 A1 | 9/2005 | Birkmeyer et al. |
| 2005/0216003 A1 | 9/2005 | Biedermann et al. |

| | | |
|---|---|---|
| 2005/0216004 A1 | 9/2005 | Schwab |
| 2005/0222570 A1 | 10/2005 | Jackson |
| 2005/0261687 A1 | 11/2005 | Garamszegi et al. |
| 2006/0025771 A1 | 2/2006 | Jackson |
| 2006/0069391 A1 | 3/2006 | Jackson |
| 2006/0084982 A1 | 4/2006 | Kim |
| 2006/0084984 A1 | 4/2006 | Kim |
| 2006/0084987 A1 | 4/2006 | Kim |
| 2006/0089644 A1 | 4/2006 | Felix |
| 2006/0100621 A1 | 5/2006 | Jackson |
| 2006/0100622 A1 | 5/2006 | Jackson |
| 2006/0111712 A1 | 5/2006 | Jackson |
| 2006/0111715 A1 | 5/2006 | Jackson |
| 2006/0129147 A1 | 6/2006 | Biedermann et al. |
| 2006/0129149 A1 | 6/2006 | Iott et al. |
| 2006/0155278 A1 | 7/2006 | Warnick |
| 2006/0161152 A1 | 7/2006 | Ensign et al. |
| 2006/0161153 A1 | 7/2006 | Hawkes et al. |
| 2006/0173456 A1 | 8/2006 | Hawkes et al. |
| 2006/0195086 A1 | 8/2006 | Sybert |
| 2006/0200128 A1 | 9/2006 | Mueller |
| 2006/0217716 A1 | 9/2006 | Baker et al. |
| 2006/0229615 A1 | 10/2006 | Abdou |
| 2006/0235392 A1 | 10/2006 | Hammer et al. |
| 2006/0235393 A1 | 10/2006 | Bono et al. |
| 2006/0241603 A1 | 10/2006 | Jackson |
| 2006/0264933 A1 | 11/2006 | Baker et al. |
| 2006/0276792 A1 | 12/2006 | Ensign et al. |
| 2006/0293659 A1 | 12/2006 | Alvarez |
| 2006/0293664 A1 | 12/2006 | Schumacher |
| 2007/0043357 A1 | 2/2007 | Kirschman |
| 2007/0043359 A1 | 2/2007 | Altarac et al. |
| 2007/0053765 A1 | 3/2007 | Warnick et al. |
| 2007/0055242 A1 | 3/2007 | Bailly |
| 2007/0090238 A1 | 4/2007 | Justis |
| 2007/0093817 A1 | 4/2007 | Barrus et al. |
| 2007/0093821 A1 | 4/2007 | Freudiger |
| 2007/0093826 A1 | 4/2007 | Hawkes et al. |
| 2007/0093831 A1 | 4/2007 | Abdelgany et al. |
| 2007/0093832 A1 | 4/2007 | Abdelgany |
| 2007/0100341 A1 | 5/2007 | Reglos et al. |
| 2007/0123862 A1 | 5/2007 | Warnick |
| 2007/0123867 A1 | 5/2007 | Kirschman |
| 2007/0162008 A1 | 7/2007 | Cline, Jr. et al. |
| 2007/0167949 A1 | 7/2007 | Altarac et al. |
| 2007/0173819 A1 | 7/2007 | Sandlin |
| 2007/0239159 A1 | 10/2007 | Altarac et al. |
| 2007/0288004 A1 | 12/2007 | Alvarez |
| 2007/0293861 A1 | 12/2007 | Rezach et al. |
| 2008/0004625 A1 | 1/2008 | Runco et al. |
| 2008/0039839 A1 | 2/2008 | Songer et al. |
| 2008/0039840 A1 | 2/2008 | Songer et al. |
| 2008/0045953 A1 | 2/2008 | Garamszegi |
| 2008/0045956 A1 | 2/2008 | Songer et al. |
| 2008/0071277 A1 | 3/2008 | Warnick |
| 2008/0086131 A1 | 4/2008 | Daly et al. |
| 2008/0097441 A1 | 4/2008 | Hayes et al. |
| 2008/0097457 A1 | 4/2008 | Warnick |
| 2008/0167689 A1 | 7/2008 | Matthis et al. |

FOREIGN PATENT DOCUMENTS

| | | |
|---|---|---|
| DE | 3639810 A1 | 5/1988 |
| DE | 3711013 C1 | 6/1988 |
| DE | 9403231 U1 | 4/1994 |
| EP | 128058 A1 | 12/1984 |
| EP | 242705 A2 | 10/1987 |
| EP | 242708 A2 | 10/1987 |
| EP | 1190678 A2 | 3/2002 |
| EP | 1210914 A1 | 5/2002 |
| EP | 1604617 A2 | 12/2005 |
| FR | 2615095 A1 | 11/1988 |
| FR | 2624720 A1 | 6/1989 |
| FR | 2706762 A1 | 12/1994 |
| FR | 2852815 A1 | 10/2004 |
| GB | 167228 A | 7/1921 |
| GB | 2173104 A | 10/1986 |
| WO | 8707134 A1 | 12/1987 |
| WO | 0152758 A1 | 6/2001 |
| WO | 02080788 A1 | 10/2002 |
| WO | 03086204 A2 | 4/2003 |
| WO | 2004103194 A1 | 5/2004 |
| WO | 2004089245 A2 | 10/2004 |
| WO | 2006047555 A2 | 5/2006 |
| WO | 2006047707 A2 | 5/2006 |
| WO | 2006047711 A2 | 5/2006 |
| WO | 2007075454 A1 | 7/2007 |
| WO | 2008008511 A2 | 1/2008 |

* cited by examiner

PEDICLE SCREW SYSTEM WITH PROVISIONAL LOCKING ASPECTS

RELATED APPLICATIONS

This application claims priority to U.S. Provisional Patent Application No. 60/723,498 titled "Pedicle Screw Systems With Provisional Locking Aspects" filed on Oct. 4, 2005, to which Applicant claims the benefit of the earlier filing and which is incorporated herein by reference in its entirety.

FIELD

The present system and method relate to bone fixation devices. More particularly, the present system and method provide for a screw assembly configured to facilitate the internal fixation of vertebral bodies while providing provisional locking aspects.

BACKGROUND

Various devices for internal fixation of bone segments in the human or animal body are known in the art. One type of system is a pedicle screw system, which is sometimes used as an adjunct to spinal fusion surgery, and which provides a means of gripping a spinal segment. A conventional pedicle screw system comprises a pedicle screw and a rod-receiving device. The pedicle screw includes an externally threaded stem and a head portion. The rod-receiving device couples to the head portion of the pedicle screw and receives a rod (commonly referred to as a distraction rod). Two such systems are inserted into respective vertebrae and adjusted to distract and/or stabilize a spinal column, for instance during an operation to correct a herniated disk. The pedicle screw does not, by itself, fixate the spinal segment, but instead operates as an anchor point to receive the rod-receiving device, which in turn receives the rod. One goal of such a system is to substantially reduce and/or prevent relative motion between the spinal segments that are being fused.

Although conventional prior art pedicle screw systems exist, they lack features that enhance and/or benefit newer, minimally invasive surgery (MIS) techniques that are more commonly being used for spinal surgeries. It has been suggested that one possible advantage of an MIS approach is that it can decrease a patient's recovery time.

Conventional pedicle screw systems and even more recently designed pedicle screw systems have several drawbacks. Some of these pedicle screw systems are rather large and bulky, which may result in more tissue damage in and around the surgical site when the pedicle screw system is installed during surgery. The prior art pedicle screw systems have a rod-receiving device that is pre-operatively coupled or attached to the pedicle screw. In addition, some of the prior art pedicle screw systems include numerous components that must all be carefully assembled together. Further, traditional pedicle screw systems are pre-operatively assembled, which makes these systems more difficult to install and maneuver in a spinal operation where MIS techniques are used.

SUMMARY

An exemplary tulip assembly configured to be coupled to a head of a bone fixation device provides a unique way to assemble and/or install a pedicle screw system by providing provisional locking aspects, one of which secures a tulip assembly onto a head portion of a pedicle screw and at least one other which permits a surgeon to easily, retainably capture a rod in the tulip assembly during a surgical operation. In one exemplary embodiment, the provisional locking aspects that secure the tulip assembly onto a head portion of a pedicle screw may be engaged independent of the locking aspects that capture a rod in the tulip. Further, the pedicle screw system described herein is easily manipulated during the surgical operation and can be robustly secured to the vertebrae and to an adjacent pedicle screw. The provisional locking aspects of the pedicle screw system provide for a robust assembly and/or installation, which may prevent or even eliminate premature failure that has been known to occur when at least some of the components of the pedicle screw system begin to slide, move, vibrate, and/or rotate relative to one another over time.

According to another exemplary embodiment, a tulip assembly configured to be coupled to a head of a bone fixation device includes at least one inner member configured to fix an angular position of the tulip assembly relative to the bone fixation device and an outer member including at least one engagement surface configured to selectively fix a rod in the tulip assembly via rotation of the outer member. According to this exemplary embodiment, the fixation of an angular position of the tulip assembly relative to the bone fixation device and the rod fixation are temporally separate operations.

According to yet another exemplary embodiment, a tulip assembly configured to be coupled to a head of a bone fixation device includes: an outer housing member including an upper portion and a lower portion having an internal tapered edge in the lower portion, a first inner member disposed in a lower portion of the outer member, the first inner member being elastically expandable to receive the head of a bone fixation device, a second inner member disposed in an upper portion of the outer member, the second inner member being configured to receive a distraction rod, wherein the first inner member includes an external tapered edge and an internal tapered edge, the external tapered edge being configured to mate with the internal tapered edge of the outer housing member to compress the first inner member independent of an actuation of the outer member.

A pedicle screw system, according to one exemplary embodiment disclosed herein, includes a pedicle screw having a threaded portion and a head portion, and a tulip assembly including at least one inner member configured to fix the tulip assembly to the head portion, and an outer member including at least one engagement surface configured to selectively fix a rod in the tulip assembly via rotation of the outer member.

Similarly, a method of fixing a tulip assembly to a pedicle screw includes inserting the pedicle screw into a bone, the pedicle screw including a head portion, expanding a first inner member over and head portion of the pedicle screw after the pedicle screw is inserted into a bone, fixing an angle of the tulip assembly relative to the pedicle screw using the first inner member and a second inner member, inserting a rod into the tulip assembly, and positionally locking the rod in the tulip assembly after the angle is fixed by rotating an outer member of the tulip assembly including at least one rod engagement surface.

Another exemplary method of fixing a tulip assembly to a pedicle screw includes inserting the pedicle screw into a bone, the pedicle screw including a head portion, expanding a first inner member over and head portion of the pedicle screw after the pedicle screw is inserted into a bone, fixing an angle of the tulip assembly relative to the pedicle screw using the first inner member and a second inner member, and positionally locking a rod in the tulip member after the angle is fixed.

BRIEF DESCRIPTION OF THE DRAWINGS

The accompanying drawings illustrate various exemplary embodiments of the present system and method and are a part of the specification. Together with the following description, the drawings demonstrate and explain the principles of the present system and method. The illustrated embodiments are examples of the present system and method and do not limit the scope thereof.

Throughout the drawings, identical reference numbers designate similar but not necessarily identical elements.

DETAILED DESCRIPTION

Figure 1:
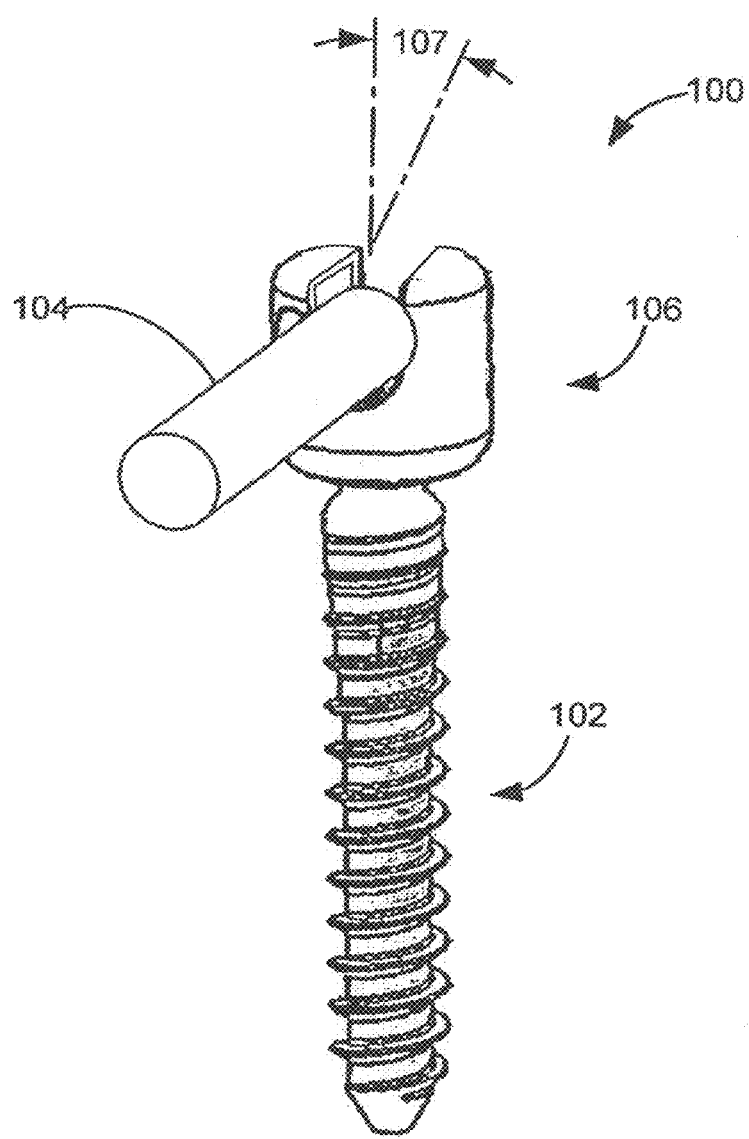
FIG. 1 is an assembled perspective view of a pedicle screw system, according to one exemplary embodiment.

The present specification describes a system and a method for separately locking the orientation of a tulip assembly relative to a pedicle screw and locking a positional location of a rod in the tulip assembly. Further, according to one exemplary embodiment, the present specification describes the structure of a tulip assembly configured to be placed on the head of a pedicle screw after placement of the pedicle screw in a patient's body and configured to receive and positionally secure a top loaded rod. Further details of the present exemplary system and method will be provided below.

By way of example, pedicle screw systems may be fixed in the spine in a posterior lumbar fusion process via minimally invasive surgery (MIS) techniques. The systems are inserted into the pedicles of the spine and then interconnected with rods to manipulate (e.g., correct the curvature, compress or expand, and/or structurally reinforce) at least portions of the spine. Using the MIS approach to spinal fixation and/or correction surgery has been shown to decrease a patient's recovery time and reduce the risks of follow-up surgeries.

The ability to efficiently perform spinal fixation and/or correction surgeries using MIS techniques is enhanced by the use of pedicle screw systems provided in accordance with the present exemplary systems and methods, which systems and methods provide a number of advantages over conventional systems. For example, a pedicle screw system in accordance with one embodiment of the present exemplary system and method provides the advantage that the pedicle screw may be inserted into the bone without being pre-operatively coupled with the rod-coupling assembly (hereinafter referred to as a tulip assembly). This is advantageous because the surgeon often needs to do other inter-body work after inserting the pedicle screw, but before attaching the larger and bulkier tulip assembly. Such an advantageous pedicle screw system may be even more crucial when using MIS techniques because the inter-body spatial boundaries in which the surgeon must work may be quite limited.

In addition, pedicle screw systems in accordance with several embodiments of the present system and method advantageously allow a user to initially fix (e.g., lock) the tulip assembly to the pedicle screw at a desired angle before inserting and/or capturing the rod. Initially locking the tulip assembly to the pedicle screw means that at least one of the components of the tulip assembly is manipulated to grip and/or clamp onto the pedicle screw to reduce and/or prevent any translational and/or rotational movement of the tulip assembly relative to the pedicle screw. The ability to initially lock the tulip assembly to the pedicle screw may facilitate the surgeon in performing compression and/or distraction of various spinal and/or bone sections.

The term "distraction," when used herein and when used in a medical sense, generally relates to joint surfaces and suggests that the joint surfaces move perpendicular to one another. However when "traction" and/or "distraction" is performed, for example on spinal sections, the spinal sections may move relative to one another through a combination of distraction and gliding, and/or other degrees of freedom.

Another advantageous feature of at least one embodiment of the present exemplary system and method is that an all-inclusive tulip assembly that can be coupled to the head portion of the pedicle screw intra-operatively is disclosed. This advantageous tulip assembly may include the aspects or features that enable the tulip assembly to be initially locked onto the head portion of the pedicle screw and then to further receive, capture, and finally lock the rod into the tulip assembly. In one exemplary embodiment, the tulip assembly is initially locked onto the head portion of the pedicle screw after the rod has been received in the tulip assembly. This advantageous tulip assembly may decrease the complexity of the pedicle screw system installation by reducing the installation to essentially a three-step process including, inserting the pedicle screw into bone, initially locking the tulip assembly onto the pedicle screw, which may be accomplished with or without the rod in the tulip assembly, and then capturing and locking the rod into the tulip assembly. In addition to accommodating the new MIS approach to spinal correction and/or fusion, the present exemplary system and method are configured to eliminate instances of cross-threading and/or post-operative tulip splaying, which occurs when the amount of stress/strain in rod, which may be caused by post-operative back flexion forces open the tulip assembly and eventually leads to the disassembly and/or the failure of the pedicle screw system.

In the following description, for purposes of explanation, numerous specific details are set forth in order to provide a thorough understanding of the present system and method for separately locking the orientation of a tulip assembly relative to a pedicle screw and a positional location of a rod in the tulip assembly. It will be apparent, however, to one skilled in the art that the present method may be practiced without these specific details. Reference in the specification to "one embodiment" or "an embodiment" means that a particular feature, structure, or characteristic described in connection with the embodiment is included in at least one embodiment. The appearance of the phrase "in one embodiment" in various places in the specification are not necessarily all referring to the same embodiment.

Exemplary Overall Structure

While the present system and method may be practiced by or incorporated into any number of bone fixation systems, the present system and method will be described herein, for ease of explanation only, in the context of a pedicle screw system. Accordingly, the present system and method includes, according to one exemplary embodiment illustrated in FIG. 1, a pedicle screw system (100) including a pedicle screw (102), a rod (104), and a coupling assembly (106), herein after referred to as a tulip assembly (106). According to one exemplary embodiment of the present system and method, the tulip assembly (106) is configured to separately lock the orientation of the tulip assembly (106) relative to the pedicle screw (102) and the positional location of the rod (104) in the tulip assembly (106). Operation of the tulip assembly (106) as well as its interaction with both the pedicle screw (102) and the rod (104) will be described in further detail below with reference to the Figures.

According to one exemplary embodiment, FIG. 1 generally shows a pedicle screw system (100) comprising a pedicle screw (102), a rod (104), and a coupling assembly (106), hereinafter referred to as a tulip assembly (106). As illustrated in FIG. 1, the pedicle screw system (100) is configured to securely couple the tulip assembly (106) to the pedicle screw (102), thereby locking or fixing the tulip assembly (106) in a relative angular position (107) relative to the pedicle screw (102). Additionally, as shown in FIG. 1, the present exemplary pedicle screw system (100) is configured to receive a rod (104) and positionally fix the rod (104) in the tulip assembly (106).

Figure 2:
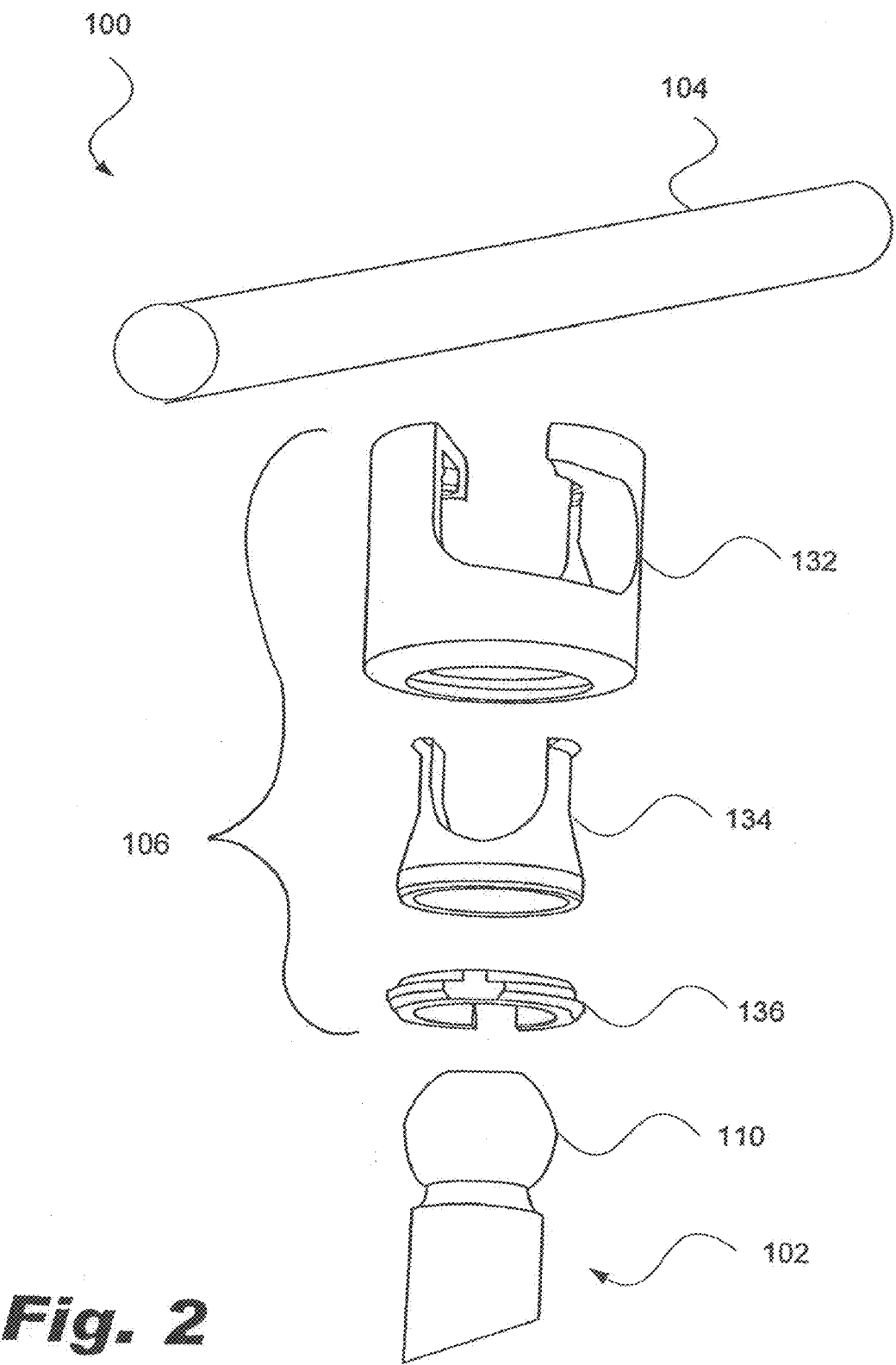
FIG. 2 is an exploded perspective view of a pedicle screw system, according to one exemplary embodiment.

FIG. 2 illustrates an exploded view of the present pedicle screw system (100), according to one exemplary embodiment. As illustrated in FIG. 2, the coupling assembly or tulip assembly (106) (FIG. 1) of the pedicle screw system (100) includes a number of components configured to perform the above-mentioned angular and positional fixing including, but in no way limited to, a tulip body (132), an inner member (134), and an expansion/contraction member (136) configured to engage the head portion (110) of the pedicle screw (102), as described in further detail below. Detailed descriptions of each component of the present pedicle screw system (100) will be described in further detail below, with reference to FIGS. 3 through 9B.

Figure 3:
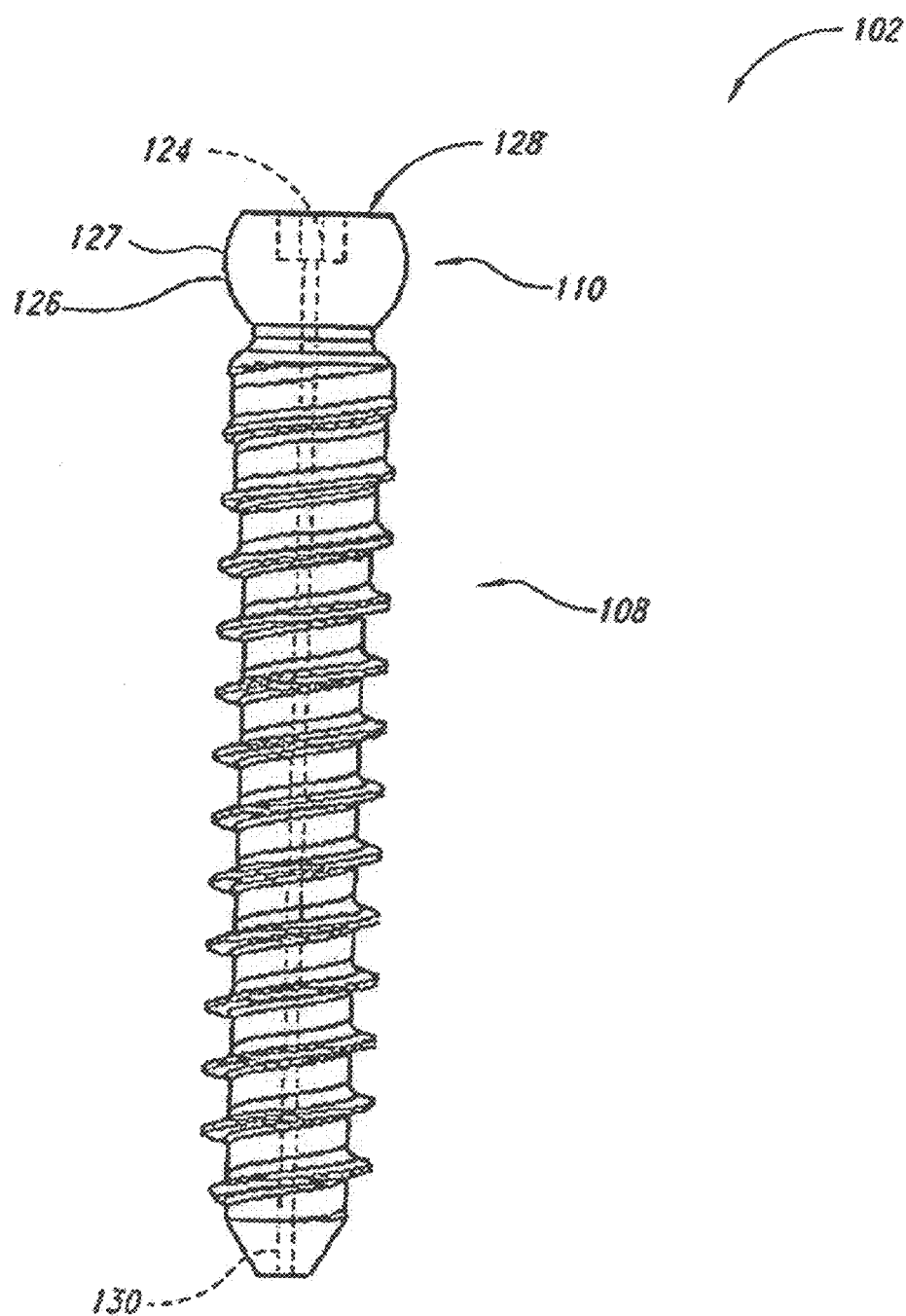
FIG. 3 is a perspective view of a pedicle screw, according to one exemplary embodiment.

FIG. 3 further illustrates the components of a pedicle screw (102), according to one exemplary embodiment. As illustrated in FIG. 3, the pedicle screw (102) includes an elongated, threaded portion (108) and a head portion (110). Although pedicle screws (102) are generally known in the art, the head portions (110) may be of varying configurations depending on what type of tulip assembly (160; FIG. 1) is to be coupled to the pedicle screw (102). The head portion (110) of the present exemplary pedicle screw (102) includes a driving feature (124) and a maximum diameter portion (126). The driving feature (124) of the present exemplary pedicle screw (102) permits the screw to be inserted into a pedicle bone and/or other bone. According to one exemplary embodiment, the pedicle bone is a part of a vertebra that connects the lamina with a vertebral body. Additionally, according to the present exemplary embodiment, the driving feature (124) can be used to adjust the pedicle screw (102) prior to or after the tulip assembly (106) is coupled to the pedicle screw (102). In the illustrated embodiment, the head portion (110) of the pedicle screw (102) is coupled to the threaded portion (108) and includes a generally spherical surface (127) with a truncated or flat top surface (128).

In one exemplary embodiment, the pedicle screw (102) is cannulated, which means a channel (130) (shown in dashed lines and extending axially through the pedicle screw (102)) extends through the entire length of the pedicle screw (102). The channel (130) allows the pedicle screw (102) to be maneuvered over and receive a Kirschner wire, commonly referred to as a K-wire. The K-wire is typically pre-positioned using imaging techniques, for example, fluoroscopy imaging, and then used to provide precise placement of the pedicle screw (102). While the pedicle screw (102) illustrated in FIG. 3 includes a number of components, numerous variations may be made including, but in no way limited to, varying the type of driving feature (124), varying materials, varying dimensions, and the like.

Figure 6:
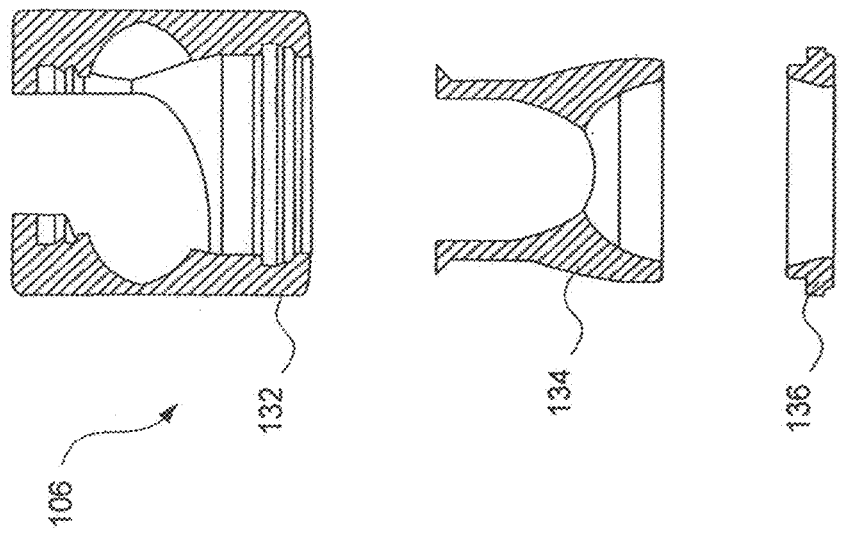
FIG. 6 is an exploded cross-sectional side view of the pedicle screw system of FIG. 4, according to one exemplary embodiment.
Figure 5:
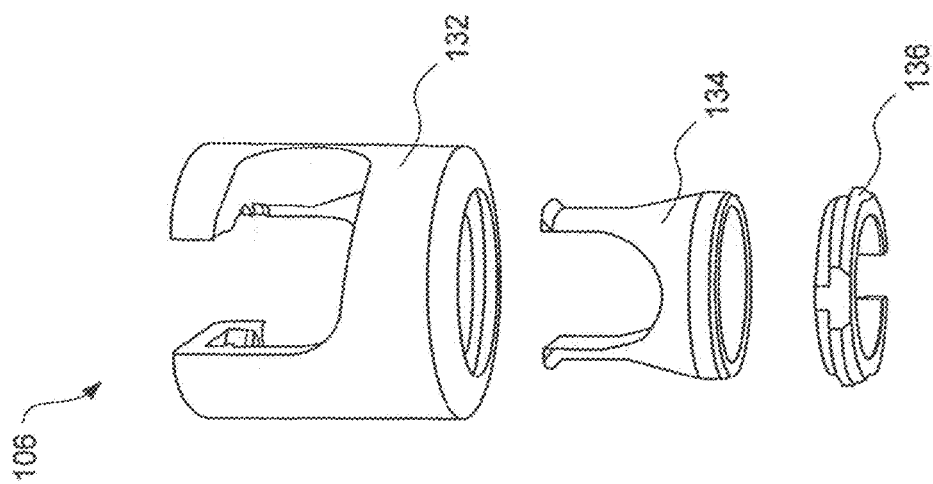
FIG. 5 is an exploded perspective view of the tulip assembly of FIG. 4, according to one exemplary embodiment.
Figure 4:
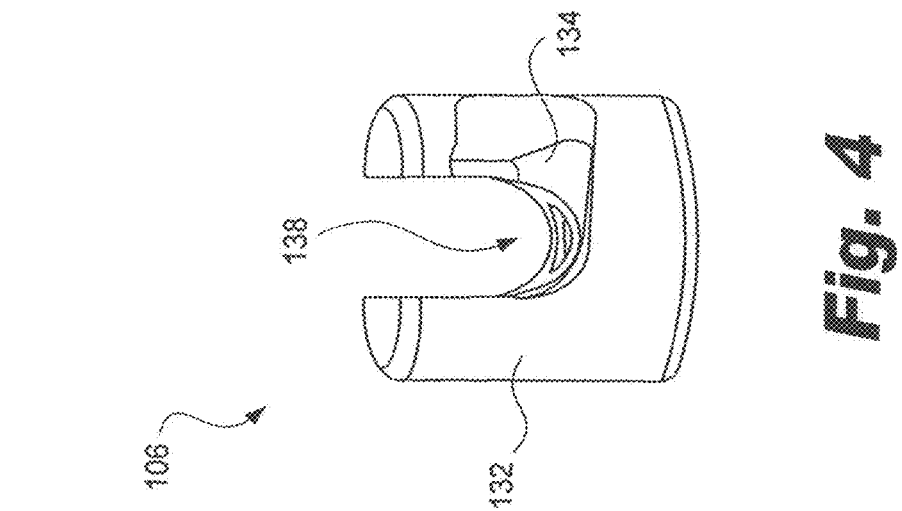
FIG. 4 is a perspective view of a tulip assembly of the pedicle screw system of FIG. 1, according to one exemplary embodiment.

Returning again to FIG. 1, the pedicle screw system includes a tulip assembly (106) configured to separately lock the orientation of the tulip assembly (106) relative to the pedicle screw (102) and the positional location of the rod (104) within the tulip assembly (106). FIGS. 4, 5, and 6 illustrate the various components of the present exemplary tulip assembly (106), according to one exemplary embodiment. FIG. 4 illustrates an assembled view of the tulip assembly (106). As illustrated in FIG. 4, the present exemplary tulip assembly (106) includes a tulip body (132) substantially housing an inner member (134) and an expansion/contraction member (not shown). Additionally, a bore (138) is defined in the center of the tulip assembly (106) to provide access to the driving feature (124; FIG. 3) of a pedicle screw (102; FIG. 3) and/or a K-wire. FIGS. 5 and 6 further illustrate an exploded assembly view and an exploded cross-sectional assembly view of the tulip assembly (106) respectively. As illustrated in FIGS. 5 and 6, the tulip body (132), the inner member (134), and the expansion/contraction member (136) each have a number of elements that work to provide the above-mentioned ability to independently lock the orientation of the tulip assembly (106) relative to the pedicle screw (102). Consequently, the exemplary configurations of the tulip body (132), the inner member (134), and the expansion/contraction member (136) will each be independently addressed in detail below with reference to FIGS. 7A through 9B.

Figure 7A:
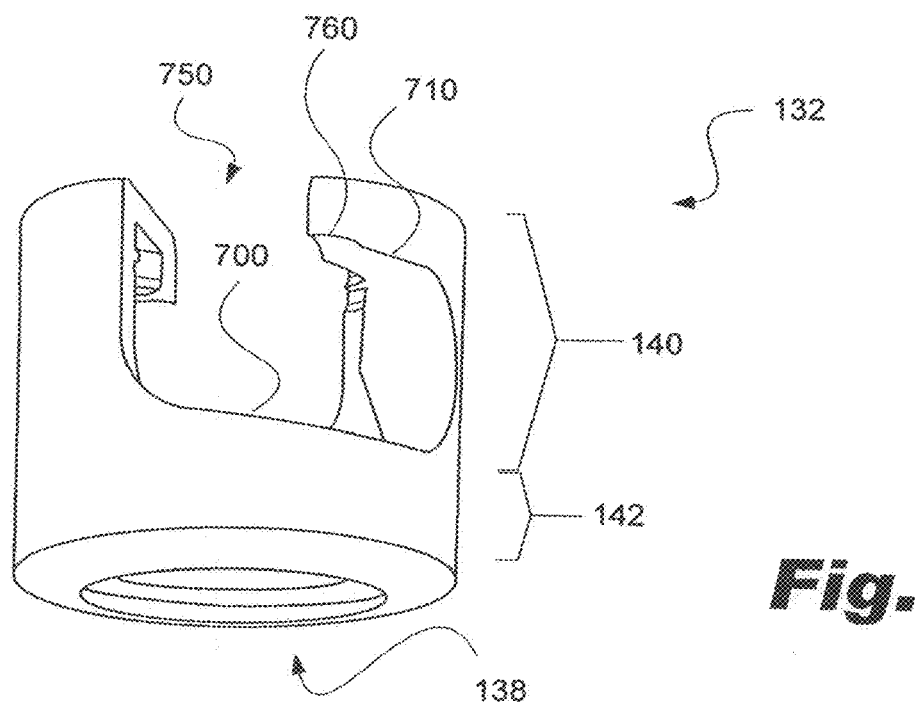
FIGS. 7A and 7B are a perspective view and a cross-sectional side-view respectively of a tulip body, according to one exemplary embodiment.
Figure 7B:
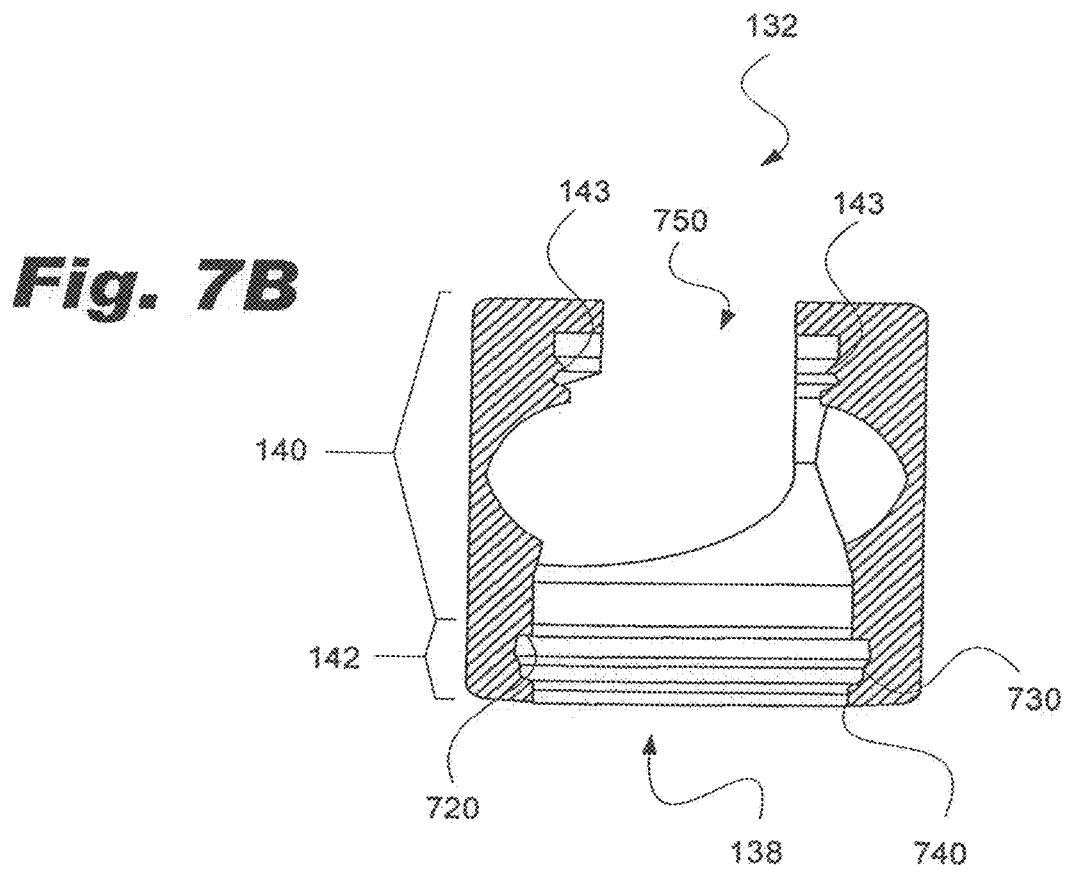

FIG. 7A illustrates a perspective view of a tulip body (132) and FIG. 7B illustrates a cross-sectional view of the tulip body (132), according to one exemplary embodiment. As illustrated in FIGS. 7A and 7B, the tulip body (132) includes a number of elements that facilitate reception of a pedicle screw head portion (110; FIG. 3) and the ability to separately lock the orientation of the tulip assembly (106; FIG. 1) relative to the pedicle screw (102; FIG. 1) and a positional location of a rod (104; FIG. 1) in the tulip assembly. According to one exemplary embodiment illustrated in FIGS. 7A and 7B, the tulip body (132) includes a bore (138), an upper portion (140), a lower portion (142), a rod reception channel (750), a declined plane (700), a rod locking surface (710), an internal lip (143), an expansion/contraction member retention lip (720), a seating bore (730), and a taper bore (740).

According to one exemplary embodiment, the bore (138) is configured to facilitate assembly of the tulip assembly (106; FIG. 4) before being placed onto the head portion of the pedicle screw (102; FIG. 1). In one embodiment, the inner member (134; FIG. 5) and the expansion/contraction member (136; FIG. 5) portion of the tulip assembly may be inserted into the tulip body (132) upward through the bore (138) or through the lower portion (142) of the tulip body (132). Additionally, once the tulip assembly (106; FIG. 4) is pre-operatively assembled, the bore (138) facilitates reception of the head portion (110; FIG. 3) of the pedicle screw (102; FIG. 3) during the initial coupling of the tulip assembly (106; FIG. 4) to the pedicle screw, as will be described in further detail below.

Continuing with FIGS. 7A and 7B, the declined plane (700), the rod reception channel, and the rod locking surface (710) of the upper portion (140) facilitate selective reception and retention of a rod (104; FIG. 1), according to one exemplary embodiment. As mentioned, the rod (104; FIG. 1) may be inserted into the tulip body (132) either before or after placement of the tulip assembly (106; FIG. 4) on the head portion (110; FIG. 3) of the pedicle screw (102; FIG. 3). Initial placement of the rod (104; FIG. 1) is received by the tulip body (132) via the rod reception channel (750). Consequently, according to one exemplary embodiment, the width of the rod reception channel (750) may be substantially equal to or greater than the diameter of a desired rod (104; FIG. 1). However, according to other exemplary embodiments, the rod reception channel (750) may be slightly narrower than the diameter of a desired rod (104; FIG. 1) to allow for a slight interference fit during insertion. Once the rod (104; FIG. 1) is received by the tulip body (132) via the rod reception channel (750), the tulip body (132) may be oriented to positionally secure the received rod (104; FIG. 1) due to both the angles of the declined plane (700) and the rod locking surface (710) as well as an interaction between the inner member (134; FIG. 5) and the rod, as will be further detailed below.

The tulip body (132) also includes a number of elements that allow the relative angular position (107; FIG. 1) of the tulip assembly (106; FIG. 4) to be independently established relative to the pedicle screw (102; FIG. 1). Specifically, the internal lip (143), the expansion/contraction member retention lip (720), the seating bore (730), and the taper bore (740) may, according to one exemplary embodiment, interact with other components of the present pedicle screw system (100) to establish the relative angular position (107; FIG. 1) of the tulip assembly (106; FIG. 4), as will be described below with reference to FIGS. 10 through 16B.

Figure 8A:
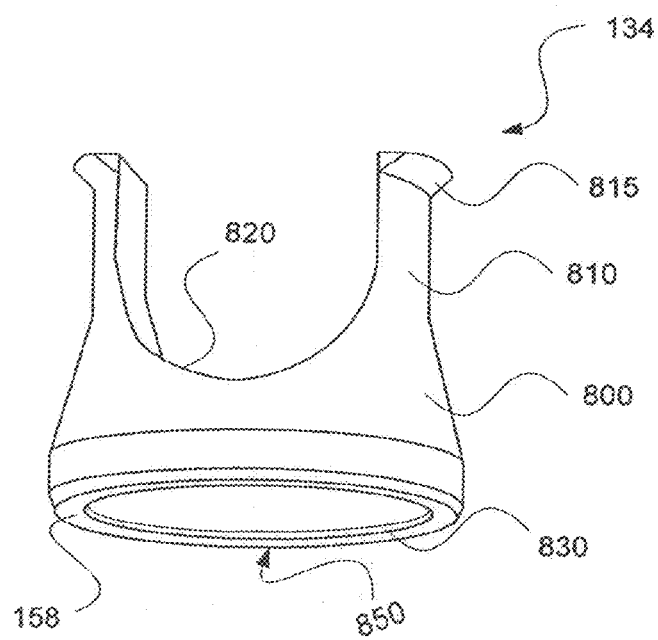
FIGS. 8A and 8B are a perspective view and a cross-sectional side-view respectively of an inner tulip member, according to one exemplary embodiment.
Figure 8B:
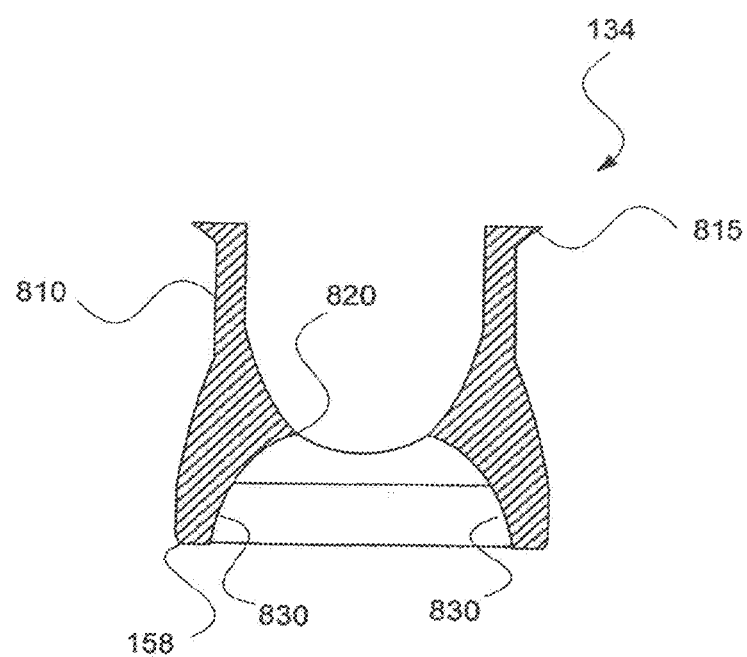

The inner member (134) of the present tulip assembly (106; FIG. 4) is illustrated in FIGS. 8A and 8B. As shown, the inner member (134) includes a main body (800) having an inner bore (850) formed therein. The inner bore (850) is substantially concentric with the bore (138; FIG. 7A) of the tulip body (132; FIG. 7A) when assembled. Additionally, the inner bore (850) is at least partially defined by the head receiving taper (830) forming an inner surface of the main body (800). Further, as illustrated in FIGS. 8A and 8B, the main body (800) includes at least one extension (810) protruding there from terminating in a positioning lip (815). The shape of the at least one extension (810) in conjunction with the main body (800) further defines a rod seat (820) configured to receive and interface with the rod (104; FIG. 2). According to one exemplary embodiment, the main body (800), the extension(s) (810), and the positioning lip (815) are all sized to be received in the bore (138) of the tulip body (132) and then be rotatable within the tulip body (132), as will be described in more detail below. The rod seat (820), along with the inner wall of the extension(s) (810), operates in cooperation with the tulip body (132) to receive, capture, and eventually positionally lock the rod (104) into the tulip assembly. The bottom surface (158) of the main body (800) may engage the expansion/contraction member (136; FIG. 5) and force the expansion/contraction member down in the bore (138; FIG. 7A) of the tulip body (132; FIG. 7A), according to one exemplary embodiment. However, according to a preferred exemplary embodiment, the bottom surface (158) of the main body (800) does not contact the expansion/contraction member (136; FIG. 5) thereby allowing the inner member to achieve its full mechanical advantage on the head portion (110; FIG. 3) of the pedicle screw (102; FIG. 3). According to this exemplary embodiment, the forced contraction of the expansion/contraction member (136; FIG. 5) along with the radial constraint provided by the seating bore (730; FIG. 7B) and the taper bore (740; FIG. 7B) of the tulip body (132; FIG. 7B), in combination with the mechanical advantage imparted by the inner member, generates sufficient radial pressure on the head portion (110; FIG. 3) of the pedicle screw (102; FIG. 3) to lock the relative angular position (107; FIG. 1) of the tulip body (132; FIG. 1) with respect to the pedicle screw (102; FIG. 1).

Figure 9A:
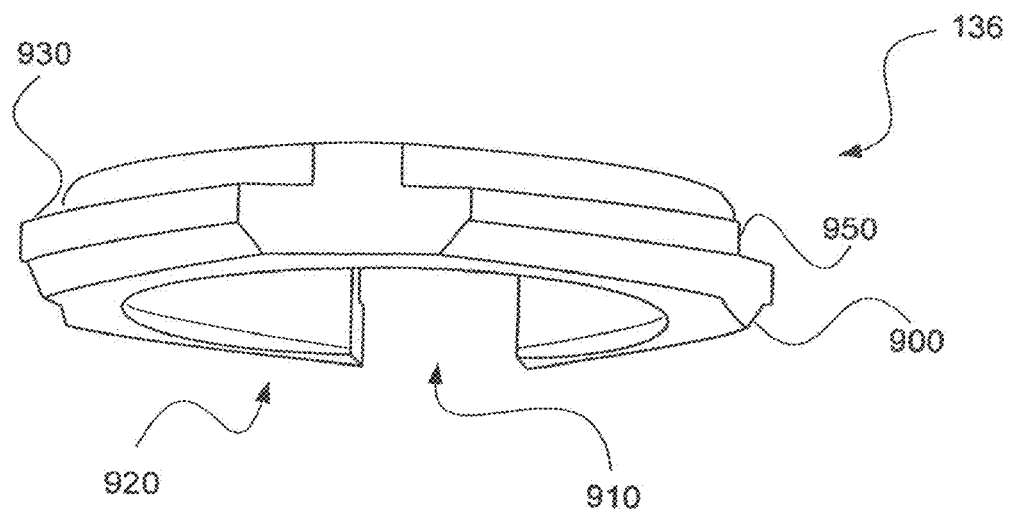
FIGS. 9A and 9B are a perspective view and a cross-sectional side-view respectively of an expansion/contraction member or split ring, according to one exemplary embodiment.
Figure 9B:
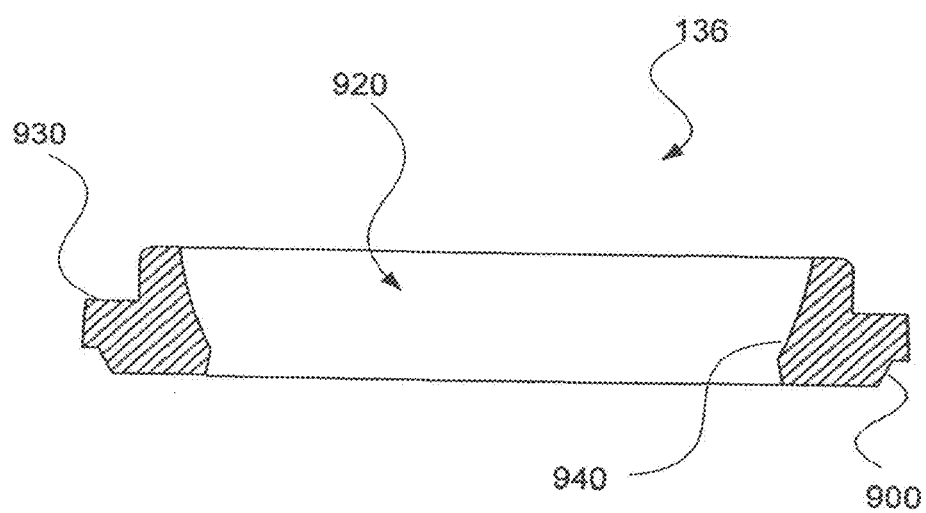

FIGS. 9A and 9B illustrate the elements of an expansion/contraction member (136), commonly referred to as a split ring. As mentioned previously, the expansion/contraction member (136) is sized and configured to be received and retained in the lower portion (142; FIG. 7A) of the tulip body (132; FIG. 7A). Accordingly, a number of features are formed on the expansion/contraction member (136) to facilitate both the insertion of the expansion/contraction member (136) into the tulip body (132; FIG. 7A) and to allow the expansion/contraction member (136) to receive the head portion (110; FIG. 3) of the pedicle screw (102; FIG. 3) while aiding in locking the relative angular position (107; FIG. 1) of the tulip body (132; FIG. 7A).

Specifically, as illustrated in FIGS. 9A and 9B, the exemplary expansion/contraction member (136) includes a main member body (950) having an expansion gap (910) formed therein. According to one exemplary embodiment, the expansion gap (910) is configured to facilitate the expansion and contraction of the expansion/contraction member (136) without causing undue stresses on the member material. In addition to the expansion gap (910), the expansion/contraction member (136) includes a lower head receiving orifice (920) that is configured to be concentrically aligned with the inner bore (850; FIG. 8A) of the inner member (134; FIG. 8A) and the bore (138; FIG. 7A) of the tulip body (132; FIG. 7A) when assembled. According to one exemplary embodiment, the lower head receiving orifice (920) includes a lower head interfacing surface (940) configured to initially receive the head portion (110; FIG. 3) of the pedicle screw (102; FIG. 3) and further be retained on the head portion of the pedicle screw by the tulip body (132; FIG. 7A) during a reduction step, as will be described in further detail below.

Additionally, as illustrated in FIGS. 9A and 9B, the expansion/contraction member (136) includes a translation stop (930) and a seating taper (900) formed in the member body (950). According to one exemplary embodiment, the translation stop (930) is formed having an outer diameter associated with the expansion/contraction member retention lip (720; FIG. 7B) formed in the tulip body (132; FIG. 7B). Consequently, as will be described below, the translation stop (930) interacts with the expansion/contraction member retention lip (720; FIG. 7B) to provide a resistance to translation of the expansion/contraction member during the insertion of the head portion (110; FIG. 3) of the pedicle screw (102; FIG. 3). Additionally, the expansion/contraction member (136) includes a seating taper (900) that coincides with the taper bore (740; FIG. 7B) of the tulip body (132; FIG. 7A). According to one exemplary embodiment, the seating taper (900) is configured to be positioned within the taper bore (740; FIG. 7B) and create a mechanical advantage sufficient to lock the relative angular position (107; FIG. 1) of the tulip body (132; FIG. 1) with respect to the pedicle screw (102; FIG. 1). Particularly, the seating taper (900) of the expansion/contraction member (136) frictionally contacts the taper bore (740; FIG. 7B) of the tulip body (132). Simultaneously, the lower head interfacing surface (940) of the expansion/contraction member (136) frictionally engages the head portion (110; FIG. 3) of the pedicle screw (102; FIG. 3), as will be described in more detail below. In one exemplary embodiment, the expansion/contraction member (136) is fabricated to be elastically expandable and contractible within the range of operations described herein. Further detail of the function and operation of the present tulip assembly (106; FIG. 4) will be described below with reference to FIGS. 10-16B.

Exemplary Implementation and Operation

Figure 10:
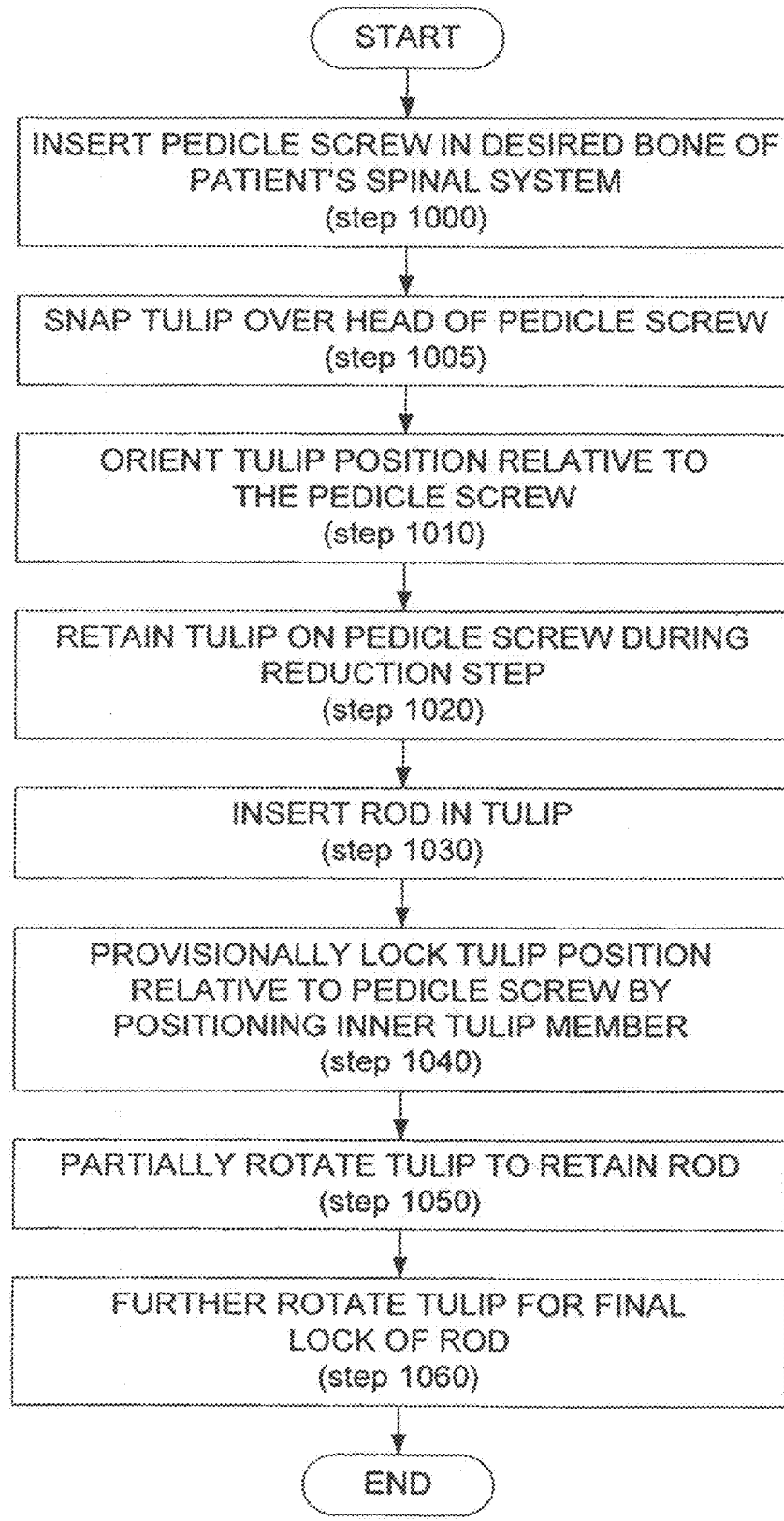
FIG. 10 is a flow chart illustrating a method for securing a tulip assembly on a pedicle screw, according to one exemplary embodiment.

FIG. 10 illustrates one method for installing the exemplary pedicle screw system (100; FIG. 1), according to one exemplary embodiment. As illustrated in FIG. 10, the present exemplary method for installing the pedicle screw system (100; FIG. 1) includes inserting one or more pedicle screws in a patient's spinal system (step 1000). Once the one or more pedicle screws are inserted in a patient's spinal system, the tulip assembly (106; FIG. 1) is installed over the head of the pedicle screw (step 1005). With the tulip assembly snapped over the head of the pedicle screw, the relative position of the tulip assembly may be oriented as desired relative to the pedicle screw (step 1010). When the desired orientation established, the tulip may be retained on the pedicle screw during a reduction step (step 1020). Once the tulip is retained, according to one exemplary embodiment, the rod may be inserted in the tulip (step 1030), and the tulip assembly position relative to the pedicle screw may be provisionally established by positioning the inner tulip member (step 1040). With the tulip position relative to the pedicle screw due to the positioning of the inner tulip member, the tulip body (132; FIG. 7B) may be partially rotated to retain the rod (step 1050) followed by a further rotation of the tulip body for a final lock of the rod (step 1060). Further details of each step of the present exemplary method will be provided below with reference to FIGS. 11 through 16B.

As illustrated in FIG. 10, the first step of the exemplary method is to insert one or more pedicle screws in a patient's spinal system (step 1000) corresponding to a desired number of pedicle screw systems (100; FIG. 1). The placement and/or number of pedicle screw systems (100; FIG. 1) to be used in a patient may be pre-operatively determined based on a pre-operative examination of the patient's spinal system using non-invasive imaging techniques known in the art, such as x-ray imaging, magnetic resonance imaging (MRI), and/or fluoroscopy imaging, for example.

Figure 11:
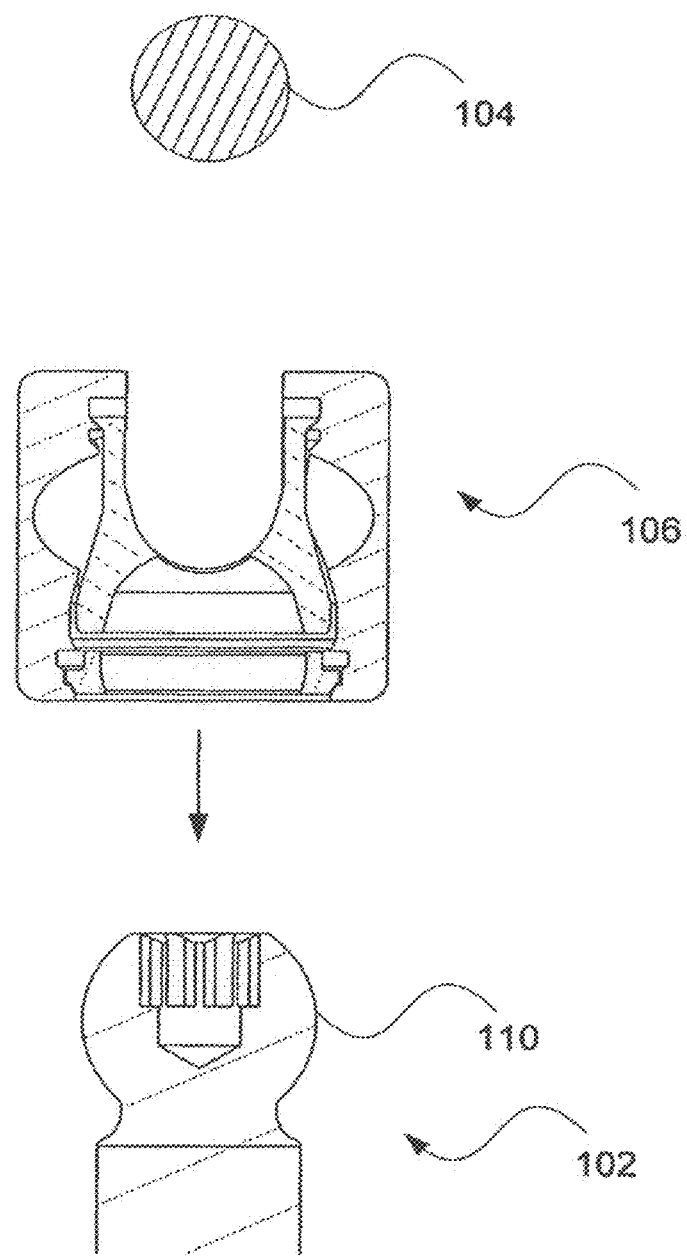
FIG. 11 is a cross-sectional side view of the components of a pedicle screw system prior to assembly, according to one exemplary embodiment.

With the one or more pedicle screws inserted into a patient's spinal system (step 1000), the tulip assembly may be snapped over the head of a previously inserted pedicle screw (step 1005), as illustrated by the arrow in FIG. 11. According to one exemplary embodiment, the tulip assembly (106) may be intra-operatively (i.e., during surgery) coupled to the head portion (110) of the pedicle screw (102) and may be maneuverable to achieve a desired placement, orientation, and/or angular position (107; FIG. 1) of the tulip assembly (106) relative to the pedicle screw (102).

Figure 12A:
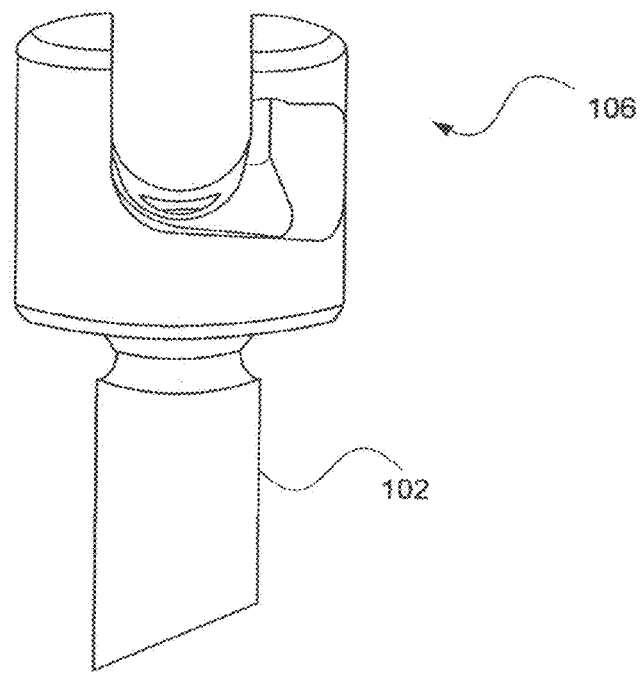
FIGS. 12A and 12B are a perspective view and a cross-sectional side-view respectively of the pedicle screw system of FIG. 10 with the tulip assembly coupled to a head of a pedicle screw, according to one exemplary embodiment.
Figure 12B:
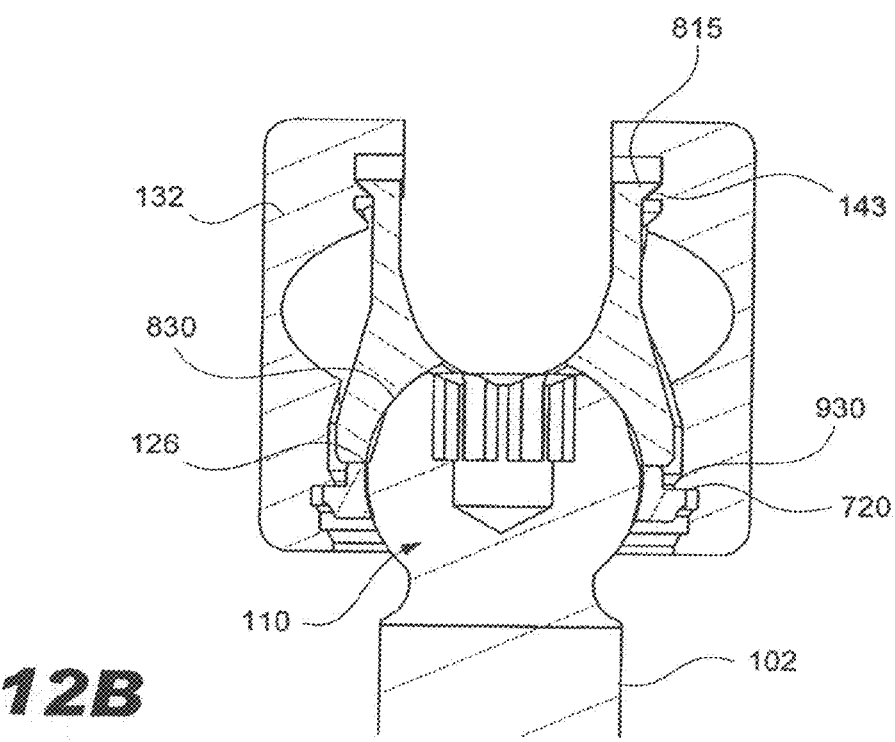

FIGS. 12A and 12B illustrate the tulip assembly (106) snapped onto the head portion (110) of the pedicle screw (102). According to one exemplary embodiment, when the tulip assembly (106) is snapped onto the head portion (110) of the pedicle screw (102), the lower head interfacing surface (940; FIG. 9B) of the expansion/contraction member (136) mates with the head portion (110) of the pedicle screw (102). As the tulip assembly (106) is pushed onto the head portion (110) of the pedicle screw (102), the expansion/contraction member (136) expands and snaps onto the head portion (110). The expansion/contraction member (136) is initially pushed up into the bore (138; FIG. 7B) of the tulip body (132), as described above. The bore (138; FIG. 7B) in the lower portion (142; FIG. 7A) of the tulip body (132) permits the expansion/contraction member (136) to float in the bore until it makes contact with the translation stop (930) as illustrated in FIG. 12B. Alternatively stated, as the expansion/contraction member (136) is pushed upwards inside of the tulip body (132) by the head portion (110) of the pedicle screw (102), the expansion/contraction member is stopped from translating and sufficient clearance is present for the expansion/contraction member to expand and snap around the head portion (110) of the pedicle screw (102). At this point of the installation method, the tulip assembly (106) may be rotationally coupled to the head portion (110) of the pedicle screw (102).

Once the tulip assembly (106) is at the desired position relative to the pedicle screw (102), the tulip assembly may then be rotated to achieve a desired orientation with respect to the pedicle screw (step 1010; FIG. 10). It is understood that the relative angular position (107; FIG. 1) of a first tulip assembly (106) to a first pedicle screw (102) may be different from the relative orientation of other pedicle screw systems (100; FIG. 1) located elsewhere on a patient's spine. In general, the relative, angular position (107; FIG. 1) of the tulip assembly (106; FIG. 1) to the pedicle screw (102) allows the surgeon to selectively and independently orient and manipulate the tulip assemblies (106) of each pedicle screw system (100; FIG. 1) installed into the patient to achieve and/or optimize the goals of the surgical procedure, which may involve compressing, expanding, distracting, rotating, reinforcing, and/or otherwise correcting an alignment of at least a portion of a patient's spine.

Figure 13A:
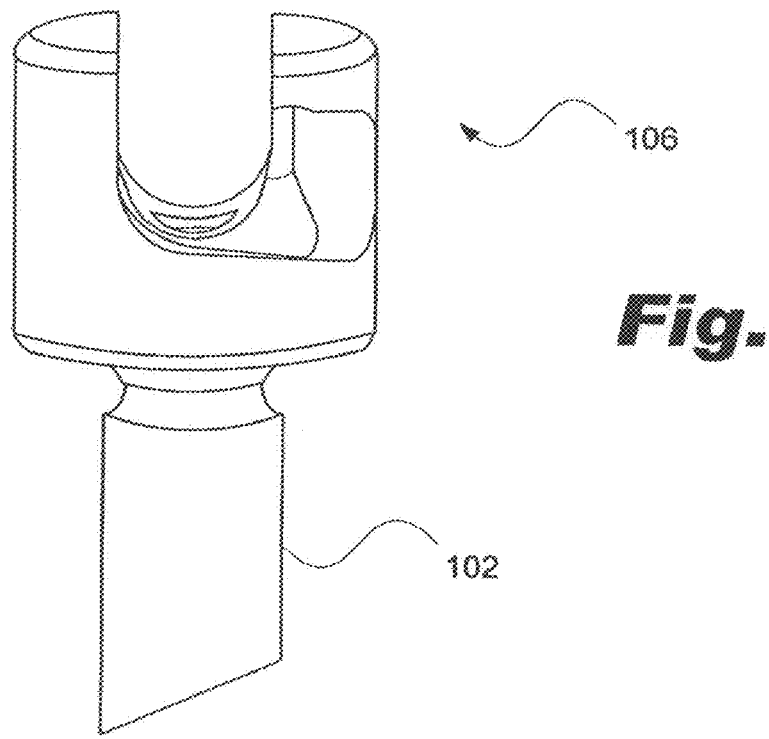
FIGS. 13A and 13B are a perspective view and a cross-sectional side-view respectively of the pedicle screw system of FIG. 10 as the tulip assembly is retained during reduction of the expansion/contraction member, according to one exemplary embodiment.
Figure 13B:
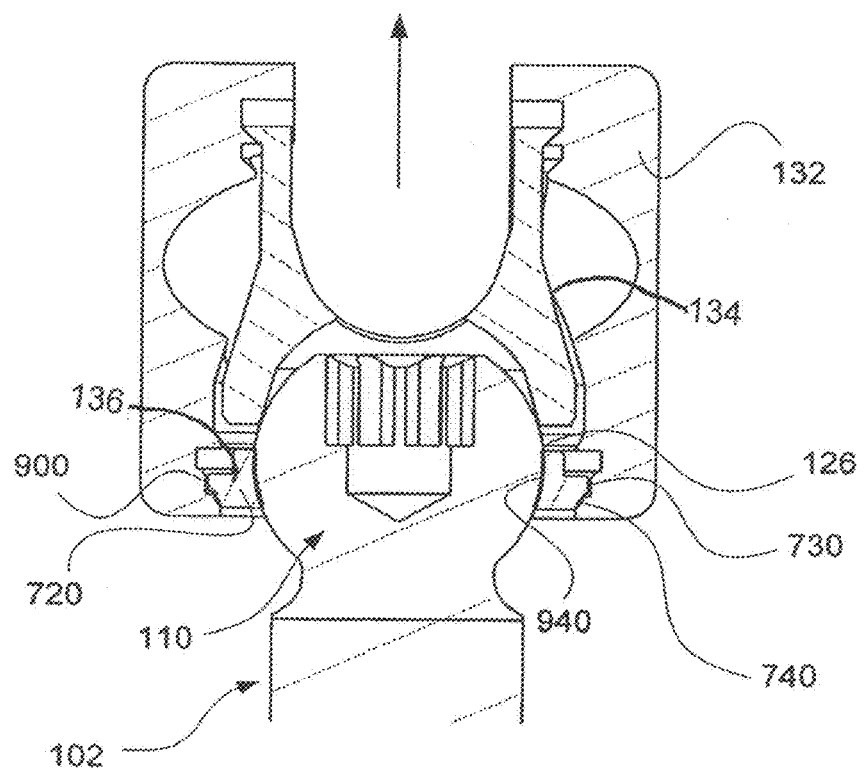

With the tulip assembly (106) positioned relative to the pedicle screw (step 1010; FIG. 10), a reduction step may be performed with the tulip assembly remaining on the pedicle screw (step 1020; FIG. 10). As illustrated in FIGS. 13A and 13B, the reduction step is performed by pulling the tulip assembly (106) away from the head portion (110) of the pedicle screw (102), as illustrated by the arrow in FIG. 13B. As the tulip assembly (106) is translated along the head portion (110), the expansion/contraction member (136) is contracted as it is seated in the seating bore (730) and the taper bore (740) of the tulip body (132). More specifically, according to one exemplary embodiment, the mating tapered surfaces, which comprise the head portion (110) of the pedicle screw (102), the lower head interfacing surface (940) and the seating taper (900) of the expansion/contraction member (136), and the seating bore (730) and taper bore (740) of the bore (138; FIG. 7) of the tulip body (132), cooperate to lock the tulip assembly (106) onto the head portion (110) of the pedicle screw.

The upward force applied to the tulip body (132), illustrated by the arrow of FIG. 13B, tends to cause compression and/or contraction of the expansion/contraction member (136) because the expansion/contraction member (136) is forced down further along the inner surface of the bore (138; FIG. 7) of the tulip body (132). Consequently, the seating taper (900) of the expansion/contraction member (136) interacts with the taper bore (740), resulting in added compression and/or contraction. Such additional compression and/or contraction of the expansion/contraction member (136) substantially locks or fixes the tulip assembly (106) onto the pedicle screw (102), thus preventing additional rotation, manipulation, loosening, and/or removal of the tulip assembly with respect to the pedicle screw. In short, when the tulip assembly (106) is initially placed onto the head portion (110) of the pedicle screw (102), the tulip assembly is free to move polyaxially in relation to the pedicle screw. Thus, the tulip assembly (106) remains free to rotate on the pedicle screw (102) until it is locked onto the head portion (110) of the pedicle screw, where the locking will be described below.

In addition, as illustrated in FIGS. 13A and 13B, both the tulip body (132) and the inner member (134) are aligned to receive the rod (104; FIG. 11). For purposes of clarity, however, the rod (104; FIG. 11) is not shown so that the features of the tulip assembly (106) that capture and lock the rod are more readily viewable. It will be understood that the tulip assembly (106) may be fixed to the pedicle screw (102) at various stages of the present exemplary installation of the pedicle screw system (100; FIG. 1). In one exemplary embodiment, the tulip assembly (106) is fixed onto the pedicle screw (102) before the rod (104; FIG. 11) is fixed or locked into the tulip assembly. In another embodiment, the tulip assembly (106) is fixed onto the pedicle screw (102) contemporaneously as the rod (104; FIG. 11) is fixed or locked into the tulip assembly. For ease of explanation, the present method will continue to be described according to the exemplary method illustrated in FIG. 10.

Figure 14A:
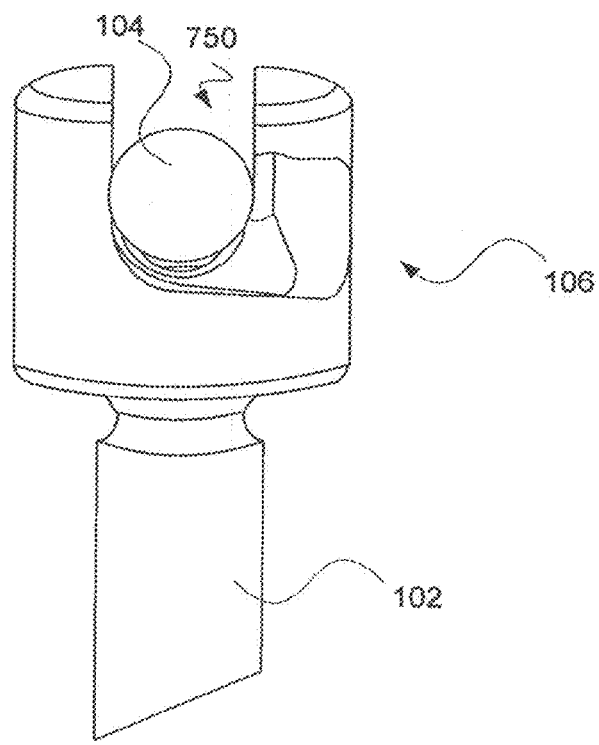
FIGS. 14A and 14B are a perspective view and a cross-sectional side-view respectively of the provisional locking of the tulip assembly, according to one exemplary embodiment.
Figure 14B:
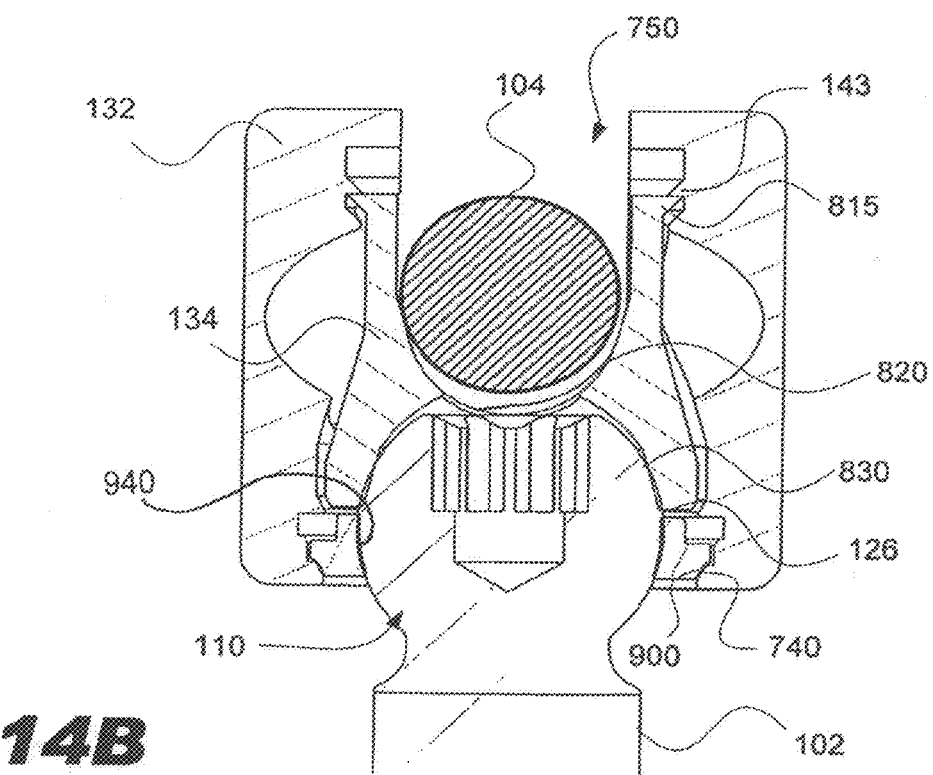

Continuing with FIGS. 14A and 14B, once the reduction of the expansion/contraction member (136) has been performed, the rod (104) may be inserted in the tulip assembly (step 1030; FIG. 10) and the tulip position relative to the pedicle screw may be provisionally locked by positioning the inner tulip member (step 1040; FIG. 10). As illustrated, the rod (104) may be placed through the rod reception channel (750) and into the rod seat portion (820) of the inner member (134). According to one exemplary embodiment, the rod reception channel (750) and the rod seat portion (820) of the inner member (134) are specifically sized to receive the rod (104) without significant interference.

With the rod (104) inserted in the rod reception channel (step 1030), the tulip position relative to the pedicle screw may be provisionally locked by positioning the inner tulip member (step 1040; FIG. 10). As illustrated in FIG. 14B, the inner member (134) may be forced toward the head portion (110) of the pedicle screw (102), either by a force translated through the rod (104), or by another instrument. As the inner member (134) is pushed toward the head portion (110) of the pedicle screw (102), the positioning lip (815) is retained under the internal lip (143) of the tulip body (132). As the inner member (134) is forced downward such that the positioning lip (815) is retained under the internal lip (143) of the tulip body, the head receiving taper (830) portion of the inner member engages the head portion (110) of the pedicle screw (102), imparting a friction inducing force thereon. According to one exemplary embodiment, the extensions (810) of the inner member (134) flex inward when pushed down and then expand to become engaged under the internal lip (143) of the tulip body (132). This longitudinal engagement to retain the inner member (134) compressed within the tulip body (132) may be accomplished either before or after the rod (104) is placed in the tulip assembly (106).

According to one exemplary embodiment, when the positioning lip (815) of the inner member (134) is placed under the internal lip (143) of the tulip body (132), the frictional force exerted on the head portion (110) of the pedicle screw (102) is maintained, provisionally locking the tulip position. According to one exemplary embodiment, the friction provided by the head receiving taper (830) portion of the inner member is greater than the friction provided by the lower head interfacing surface (940) and the seating taper (900) of the expansion/contraction member (136). This variation of friction between the lower head interfacing surface (940) and the head receiving taper (830) prevents screw advancement when the outer housing is rotated for rod locking, as is described below. According to one exemplary embodiment, the variation of friction between the lower head interfacing surface (940) and the head receiving taper (830) is achieved by varying their respective tapers, and consequently, varying the mechanical advantage achieved by each.

Figure 15A:
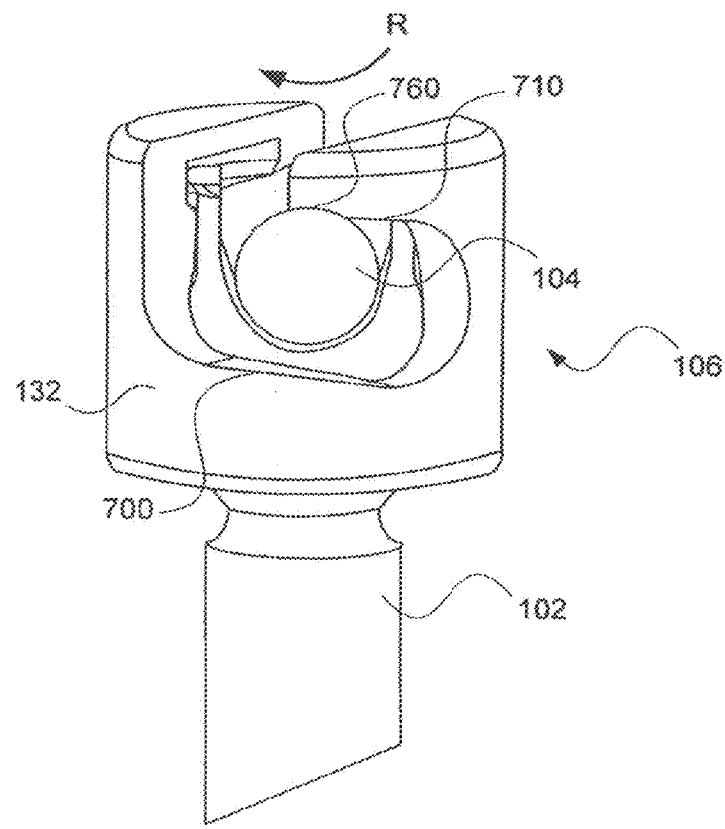
FIGS. 15A and 15B are a perspective view and a cross-sectional side-view respectively of the rotation of the tulip body to retain a rod, according to one exemplary embodiment.
Figure 15B:
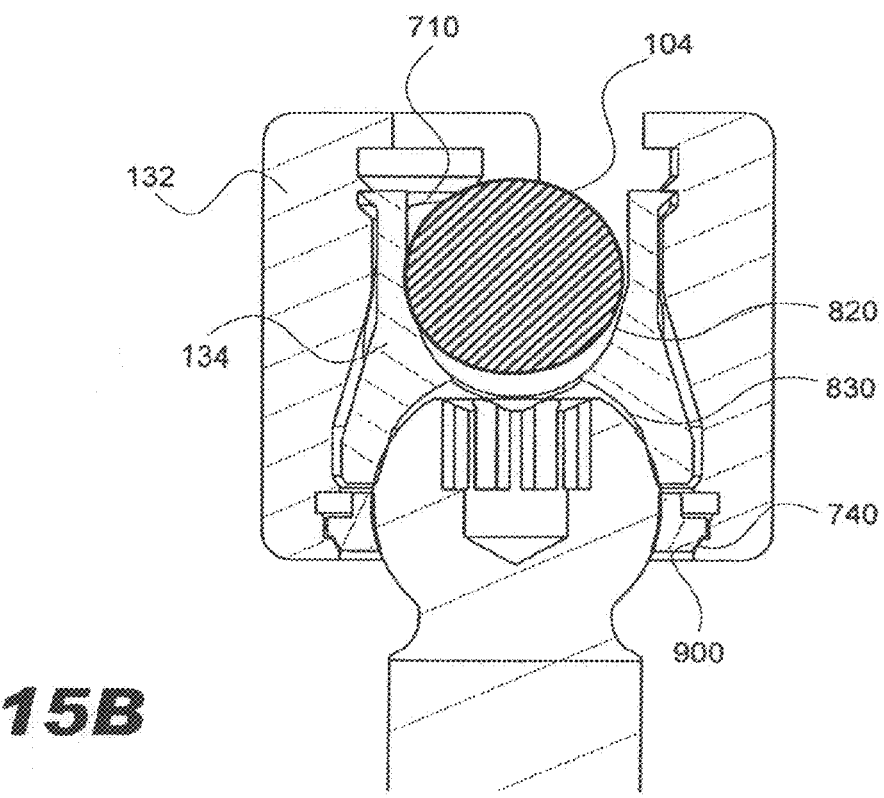

With the position of the tulip assembly (106) relative to the pedicle screw (102) established, the tulip body (132) may be partially rotated to substantially retain the rod (step 1050; FIG. 10). More particularly, as illustrated in FIGS. 15A and 15B, the tulip body (132) may be rotated, as indicated by the arrow R, causing the rod locking surface (710) of the tulip body (132) to engage the rod (104). According to one exemplary embodiment, an angular rotation of approximately 30 degrees is sufficient to substantially retain the rod (step 1050; FIG. 10) within the tulip assembly (106). The rod (104) may initially be retained on the rod-capturing portion (760) (best shown in FIG. 7A) of the rod locking surface (710), according to one exemplary embodiment. In addition, after the tulip body (132) is partially rotated to capture the rod (104), the rod locking surface (710), and particularly the rod-capturing portion (760) of the tulip body (132) prevent the tulip body (132) from splaying open under operative and post-operative dynamic and static loading, for example. Splaying is prevented due to the increased amount of tulip body material that is coupled up and over the rod (104), compared to traditional pedicle screw assemblies. When the tulip body (132) is rotated, the rod locking surface (710) engages the rod (104) and creates sufficient interference with the rod to prevent the rod from slideably translating through the tulip assembly (106). The interference is caused, according to one exemplary embodiment, between at least the rod (104), the rod locking surface (710) of the tulip body (132), and the rod seat portion (820) of the inner member (134).

Figure 16A:
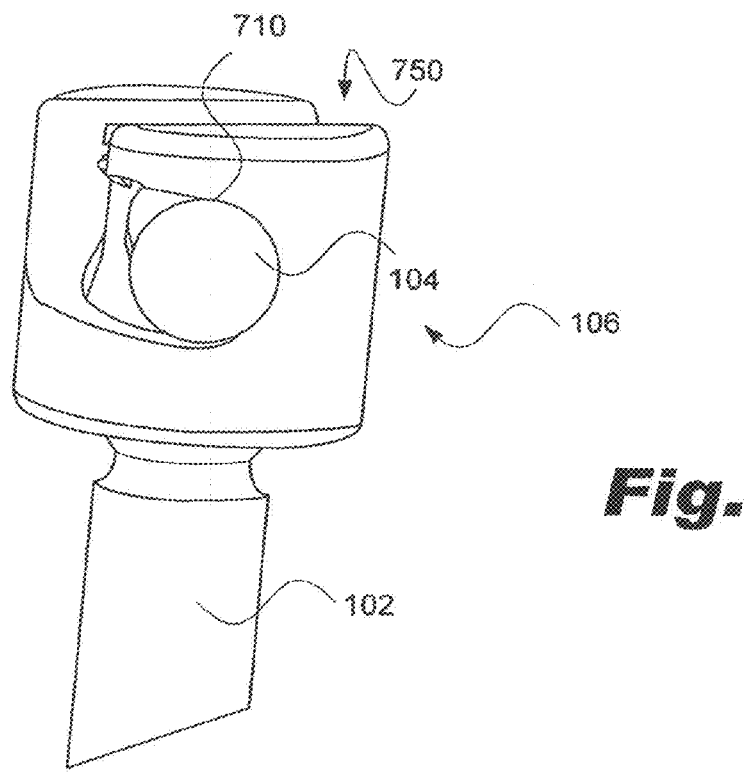
FIGS. 16A and 16B are a perspective view and a cross-sectional side-view respectively of the rotation of the tulip body to finally lock the rod, according to one exemplary embodiment.
Figure 16B:
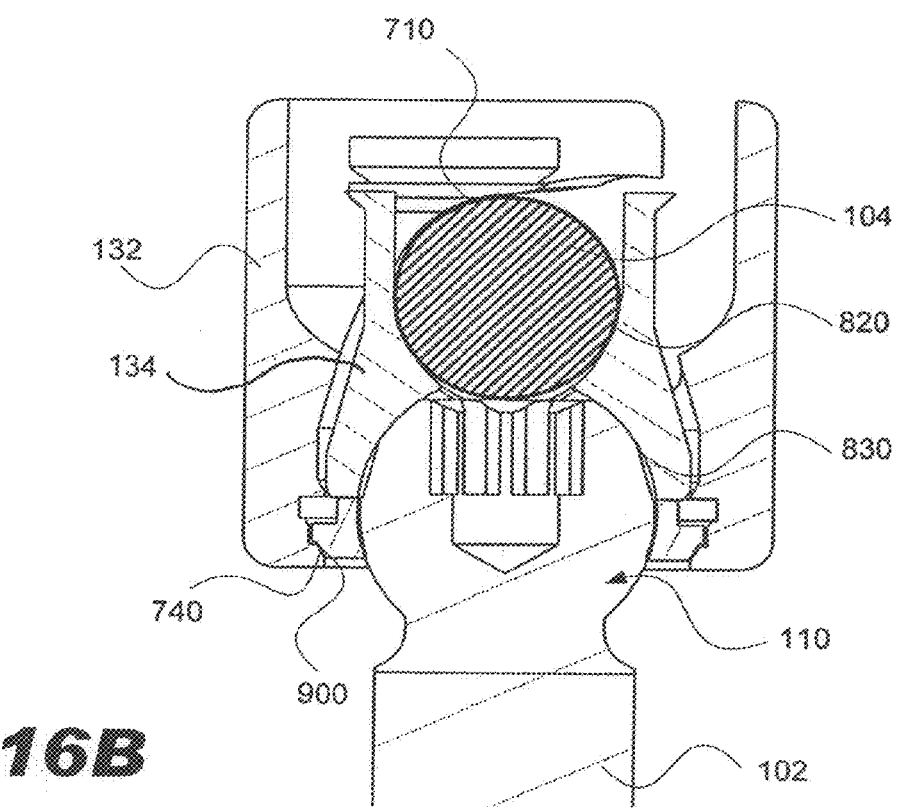

As the tulip body (132) is further rotated, as illustrated in FIGS. 16A and 16B, the rod is placed in a final lock position within the tulip assembly (step 1060). According to one exemplary embodiment, as the tulip body (132) is further rotated, the rod locking surface (710) continues to force the rod (104) into the rod seat (820) of the inner member (134). As illustrated in the exemplary embodiment of FIG. 16B, when in the final lock position, the rod (104) is forced into substantially full engagement with the rod seat (820). Consequently, the resistive force exerted against the rod (104) increases the frictional resistance provided by the rod locking surface (710) to prevent the rod from slideably translating within the tulip assembly (106). Additionally, the increased engagement between the rod seat (820) and the rod (104) further forces the head receiving taper onto the head portion (110) of the pedicle screw (102), and increases the interaction between the taper bore (740) and the seating taper (900) such that the position of the tulip assembly (106) relative to the pedicle screw (102) is further secured. According to one exemplary embodiment, the rotation of the tulip body (132) may be performed by inserting an instrument into the rod reception channel (750) and forcing rotation thereof. Alternatively, the tulip body (132) may be independently rotated to secure the rod (104) within the tulip assembly (106) by any number of methods including, but in no way limited to, a socket-type tool that engages the upper outer surface of the tulip body (132).

During operation, the present exemplary pedicle screw system as described, but not limited to the embodiments herein, is designed for fixation of bone material and/or bone segments during a surgical procedure, such as fusing spinal segments in which MIS techniques are employed. For example, according to one exemplary embodiment, the pedicle screw system is inserted into the pedicles of a patient's spine and then interconnected with rods to provide support to the spine to allow for post-operative fusion of the spinal segments. While the pedicle screw can be inserted with the tulip assembly coupled with the pedicle screw, one embodiment for the installation of the pedicle screw system includes inserting the pedicle screw into the bone and subsequently coupling the tulip assembly to the pedicle screw, where such an approach has advantages over currently known pedicle screw system assemblies and/or installations.

In addition, according to a number of exemplary embodiments, various structural features of the pedicle screw system as described, but not limited to the embodiments herein, may provide other advantages over existing pedicle screw systems. First, the pedicle screw may be inserted into the bone of a patient without the presence of the tulip assembly or rod, which permits the surgeon to place the screw and then perform subsequent inter-body work without having to work around the tulip assembly or the rod. Second, the tulip assembly includes a mechanism for capturing the rod that eliminates problems associated with conventional pedicle screws, such as cross-threading, because the exemplary pedicle screw systems disclosed herein do not use any threads to couple the tulip assembly to the pedicle screw or to capture and lock the rod into the tulip assembly. Third, the interface between the head portion of the pedicle screw and the tulip assembly provide an initial lock, which allows the angle of the tulip assembly to be set or fixed with respect to the pedicle screw before insertion of the rod and/or before the rod is captured in the tulip assembly. With this type of pedicle screw system, the surgeon has the ability to check and even double check the placement, angle, and/or orientation regarding aspects of the pedicle screw system to facilitate, and even optimize, the compression, distraction, and/or other manipulation of the spinal segments. Further, the present exemplary pedicle screw system accommodates the new MIS techniques being applied to spinal operations.

One possible post-operative advantage of the present exemplary pedicle screw system is that the cooperation and interaction of the inner member with the tulip body of the tulip assembly substantially reduces, and most likely prevents, the known problem of tulip splaying. Tulip splaying is generally regarded as a post-operative problem caused by a stressed rod forcing open portions of the tulip body, which eventually leads to the disassembly and likely failure of the pedicle screw system within the patient. Yet another post-operative advantage of the pedicle screw systems is that unlike existing rod-coupling members or constructs, the exemplary tulip assemblies described herein have a smaller size envelope (e.g., less bulky, lower profile, and/or more compact shape) and are easier to place onto the pedicle screw, when compared to traditional tulip assemblies. The smaller size and ease of installation may reduce trauma to the soft-tissue regions in the vicinity of the surgical site, which in turn generally allows for a quicker recovery by the patient. Yet another possible advantage of the present exemplary pedicle screw system over traditional existing systems is that all of the parts needed to lock the tulip assembly to the pedicle screw and to capture and lock the rod into the tulip assembly are included within the tulip assembly. Accordingly, once the tulip assembly is snapped or otherwise coupled to the pedicle screw, no additional locking cap or threaded fastener is needed to complete the assembly/installation of the pedicle screw system. According to aspects described herein, and as appended by the claims, the present exemplary pedicle screw systems permit insertion of the pedicle screw without the tulip assembly coupled thereto, locking the tulip assembly onto the pedicle screw, and subsequently capturing and locking the rod into the tulip assembly.

The preceding description has been presented only to illustrate and describe the present method and system. It is not intended to be exhaustive or to limit the present system and method to any precise form disclosed. Many modifications and variations are possible in light of the above teaching.

The foregoing embodiments were chosen and described in order to illustrate principles of the system and method as well as some practical applications. The preceding description enables others skilled in the art to utilize the method and system in various embodiments and with various modifications as are suited to the particular use contemplated. It is intended that the scope of the present exemplary system and method be defined by the following claims.

What is claimed is:

1. A tulip assembly configured to be coupled to a head of a bone fixation device comprising:
   at least one inner member configured to fix said tulip assembly to said head of a bone fixation device; and
   an outer member having a rod-reception channel and a rod seat both of which are adapted to receive a rod, said outer member comprising at least one engagement surface in communication with said rod-reception channel, said at least one engagement surface configured to selectively fix said rod in the tulip assembly via rotation of said outer member;
   wherein said at least one inner member is configured to positionally fix said tulip assembly relative to said head of said bone fixation device in response to movement of said at least one inner member in said outer member and relative to said head and independent of said rotation of said outer member, said rod-reception channel being adapted to receive said rod after said at least one inner member is fixed onto said head, said rod-reception channel having a portion that extends axially and a second portion that extends circumferentially about an axis of said outer member;

wherein during said rotation of said outer member, said at least one engagement surface engages said rod and causes said rod to move in said rod-reception channel and locks said rod in said rod seat.

2. The tulip assembly of claim 1, wherein said at least one engagement surface comprises a declining plane configured to force said rod into said at least one inner member when said outer member is rotated.

3. The tulip assembly of claim 1, wherein said at least one inner member comprises:
a first inner member disposed in a lower portion of said outer member;
a second inner member disposed in an upper portion of said outer member;
wherein said first inner member is elastically expandable to receive said head of a bone fixation device; and
wherein said second inner member is configured to interact with said rod when said outer member is rotated.

4. The tulip assembly of claim 3, wherein said second inner member comprises:
a main body;
at least one extension proximally protruding from said main body and terminating in a positioning lip;
an inner bore formed in a distal end of said main body; and
a friction inducing taper formed on an inner wall of said main body defined by said inner bore;
wherein said friction inducing taper is configured to engage said head of a bone fixation device to fix a position of said tulip assembly relative to said bone fixation device.

5. The tulip assembly of claim 4, wherein said at least one extension defines a seat configured to receive said rod.

6. The tulip assembly of claim 4, wherein:
said outer member comprises an inner bore including an internal lip circumferentially disposed in said upper portion of said outer member;
wherein said internal lip is configured to receive said positioning lip of said second inner member when engaged to positionally secure said second inner member in said outer member.

7. The tulip assembly of claim 4, wherein said first inner member comprises a ring configured to be elastically, diametrically expandable and contractible.

8. The tulip assembly of claim 7, wherein said ring includes a split that permits a diameter of the ring to vary from a first, larger diameter to a second, smaller diameter.

9. The tulip assembly of claim 4, wherein said first inner member further comprises:
a friction inducing tapered inner surface configured to seat against said head of said bone fixation device, said bone fixation device being a pedicle screw; and
an external seating taper surface configured to induce contraction of said first inner member when interacting with a taper bore of said tulip assembly.

10. The tulip assembly of claim 9, wherein said friction inducing tapered inner surface and said friction inducing taper of said second inner member have different taper angles.

11. The tulip assembly of claim 10, wherein said friction inducing taper of said second inner member imparts a greater frictional force on said head of a bone fixation device than said friction inducing tapered inner surface of said first inner member.

12. A tulip assembly configured to be coupled to a head of a bone fixation device comprising:

an outer housing member including an upper portion and a lower portion having an internal tapered edge in said lower portion;
a first inner member disposed in a lower portion of said outer housing member, said first inner member being elastically expandable to receive said head of a bone fixation device;
a second inner member disposed in an upper portion of said outer housing member, said second inner member being configured to receive a distraction rod; and
wherein said first inner member includes an external tapered edge and an internal tapered edge, said external tapered edge being configured to mate with said internal tapered edge of said outer housing member to compress said first inner member;
wherein said first inner member is configured to engage said head in order to fix said outer housing member to said head and said outer housing member having a rod-reception channel having a rod seat and at least one rod-engagement surface associated with said rod-reception channel, said at least one rod-engagement surface forcing said rod into said rod seat and locking said rod to said outer housing member in response to the rotation of said outer housing member, said first inner member being actuated independent of an actuation of said outer housing member or said second inner member.

13. The tulip assembly of claim 12, wherein:
said internal tapered edge of said first inner member is configured to engage a lower portion of said head of a bone fixation device;
said second inner member comprises an internal tapered edge to engage an upper portion of said head of a bone fixation device; and
wherein said internal tapered edge of said first inner member and said internal tapered edge of said second inner member create a mechanical advantage to maintain an angle of said tulip assembly relative to said bone fixation device.

14. The tulip assembly of claim 13, wherein said mechanical advantage created by said internal tapered edge of said first inner member is less than said mechanical advantage created by said internal tapered edge of said second inner member.

15. The tulip assembly of claim 13, wherein said second inner member further comprises an engagement portion in contact with said first inner member to maintain a contraction of said first inner member.

16. The tulip assembly of claim 15, wherein:
said outer housing member comprises an inner bore including an internal lip circumferentially disposed in said upper portion of said outer housing member; and
wherein said second inner member further comprises at least one positioning lip configured to engage said internal lip of said outer housing member to maintain an engaged position of said second inner member.

17. The tulip assembly of claim 13, wherein said first inner member is further configured to fix said tulip assembly to said head of a bone fixation device after expanding to receive said head.

18. The tulip assembly of claim 13, wherein said outer housing member further comprises:
at least one engagement surface configured to selectively fix a rod in the tulip assembly via rotation of said outer housing member;
said at least one engagement surface including a decline plane that forces said rod into said second inner member when said outer housing member is rotated.

19. The tulip assembly of claim 18, wherein said at least one engagement surface is further configured to force said second inner member into said head of a bone fixation device, further seating said first inner member when said outer housing member is rotated while a rod is present in said tulip assembly.

20. A tulip assembly configured to be coupled to a head of a bone fixation device comprising:
  at least one inner member configured to fix an angular position of said tulip assembly relative to said bone fixation device; and
  an outer member having a rod-reception channel and a rod seat both of which are adapted to receive a rod, said outer member comprising at least one engagement surface in communication with said rod-reception channel, said at least one engagement surface configured to selectively fix said rod in the tulip assembly via rotation of said outer member;
  wherein said fixation of an angular position of said tulip assembly relative to said bone fixation device and said rod fixation are independent operations;
  wherein said at least one inner member is configured to positionally fix said tulip assembly relative to said head of said bone fixation device in response to movement of said at least one inner member in said outer member and relative to said head and independent of said rotation of said outer member, said rod-reception channel being adapted to receive said rod after said at least one inner member is fixed onto said head, said rod-reception channel having a portion that extends axially and a second portion that extends circumferentially about an axis of said outer member;
  wherein during said rotation of said outer member, said at least one engagement surface engages said rod and moves said rod until said at least one engagement surface causes said rod to move in said rod-reception channel and locks said rod in said rod seat.

21. A method of fixing a tulip assembly to a pedicle screw, said tulip assembly having an outer member, a first inner member and a second inner member situated therein comprising:
  expanding said first inner member over a head portion of said pedicle screw after said pedicle screw is inserted into a bone;
  fixing an angle of said tulip assembly relative to said pedicle screw using said first inner member and a second inner member;
  locking said first inner member to said head portion by forcing said first inner member against said head portion;
  situating a rod in a rod-reception channel of said outer member; and
  positionally locking said rod in said tulip assembly after said angle is fixed by rotating said outer member until said rod is captured in a rod seat of said rod-reception channel;
  wherein said steps of fixing of said angle of said tulip assembly relative to said pedicle screw and said positionally locking of said rod in said tulip assembly are separate and independent operations.

* * * * *

UNITED STATES PATENT AND TRADEMARK OFFICE
CERTIFICATE OF CORRECTION

| | | |
|---|---|---|
| PATENT NO. | : 7,686,835 B2 | Page 1 of 1 |
| APPLICATION NO. | : 11/543348 | |
| DATED | : March 30, 2010 | |
| INVENTOR(S) | : David R. Warnick | |

It is certified that error appears in the above-identified patent and that said Letters Patent is hereby corrected as shown below:

In Column 6, Line 15, please delete "160" and insert -- 106 -- therefor.

In Column 7, Line 67, please delete "," and insert -- . -- therefor.

In Column 9, Line 55, before the word established, please insert -- is --.

In Column 15, Line 19, please delete "a" and insert -- the -- therefor.

In Column 15, Line 31, please delete "a" and insert -- the -- before the word bone.

In Column 16, Line 6, please delete "a" and insert -- said -- therefor.

Signed and Sealed this
Twenty-fifth Day of October, 2011

David J. Kappos
*Director of the United States Patent and Trademark Office*